US011628166B2

(12) United States Patent
Moore et al.

(10) Patent No.: US 11,628,166 B2
(45) Date of Patent: *Apr. 18, 2023

(54) THERAPEUTIC USES OF COMPOUNDS HAVING COMBINED SERT, 5-HT3 AND 5-HT1A ACTIVITY

(71) Applicant: H. Lundbeck A/S, Valby (DK)

(72) Inventors: Nicholas Moore, Ridgewood, NJ (US); Marianne Dragheim, Vedbæk (DK)

(73) Assignee: H. Lundbeck A/S, Valby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/930,014

(22) Filed: May 12, 2020

(65) Prior Publication Data
US 2021/0093631 A1 Apr. 1, 2021

Related U.S. Application Data

(63) Continuation of application No. 15/661,392, filed on Jul. 27, 2017, now abandoned, which is a continuation of application No. 15/043,167, filed on Feb. 12, 2016, now Pat. No. 9,744,166, which is a continuation of application No. 12/741,780, filed as application No. PCT/DK2008/050271 on Nov. 12, 2008, now Pat. No. 9,278,096.

(60) Provisional application No. 60/987,710, filed on Nov. 13, 2007, provisional application No. 61/013,722, filed on Dec. 14, 2007, provisional application No. 61/097,840, filed on Sep. 17, 2008.

(30) Foreign Application Priority Data

Nov. 13, 2007 (DK) .................................. 200701607
Dec. 14, 2007 (DK) .................................. 200701788
Sep. 17, 2008 (DK) .................................. 200801300

(51) Int. Cl.
A61K 31/495 (2006.01)

(52) U.S. Cl.
CPC .................................. *A61K 31/495* (2013.01)

(58) Field of Classification Search
CPC .................................................. A61K 31/495
See application file for complete search history.

(56) References Cited

U.S. PATENT DOCUMENTS

| | | | |
|---|---|---|---|
| 5,258,387 A | 11/1993 | Burner | |
| 7,138,407 B2 | 11/2006 | Ruhland et al. | |
| 7,144,884 B2 * | 12/2006 | Ruhland | C07D 211/20 514/255.03 |
| 8,476,279 B2 | 7/2013 | Bang-Andersen | |
| 8,664,225 B2 * | 3/2014 | Moore | A61P 25/26 514/255.03 |
| 8,969,355 B2 * | 3/2015 | Bang-Andersen | A61P 25/16 514/255.03 |
| 9,125,908 B2 * | 9/2015 | Bang-Andersen | A61P 25/32 |
| 9,125,909 B2 * | 9/2015 | Bang-Andersen | A61P 11/16 |
| 9,125,910 B2 * | 9/2015 | Bang-Andersen | A61P 29/00 |
| 9,227,946 B2 * | 1/2016 | Faldt | A61P 19/06 |
| 9,278,096 B2 * | 3/2016 | Dragheim | A61P 25/00 |
| 9,744,166 B2 * | 8/2017 | Moore | A61P 25/20 |
| 9,861,630 B1 * | 1/2018 | Faldt | A61K 9/2059 |
| 2005/0014740 A1 | 1/2005 | Ruhland et al. | |
| 2006/0019938 A1 | 1/2006 | Beer et al. | |
| 2011/0201617 A1 | 8/2011 | Moore et al. | |
| 2012/0189697 A1 | 7/2012 | Hojer et al. | |
| 2016/0083359 A1 | 3/2016 | Bang-Andersen et al. | |

FOREIGN PATENT DOCUMENTS

| | | |
|---|---|---|
| WO | WO 2003/029232 | 4/2003 |
| WO | WO 2004/087156 | 10/2004 |
| WO | WO 2007/144005 | 12/2007 |
| WO | WO 2008/113359 | 11/2008 |

OTHER PUBLICATIONS

Communication pursuant to Article 94(3) EPC, for EP Application No. 11 193 237.2 dated Dec. 18, 2013, 5 pages.
Communication pursuant to Article 94(3) EPC, for EP Application No. 11 193 237.2 dated Mar. 24, 2014, 7 pages.
Grounds of Appeal to the decision of the Opposition Division and claims AR1-AR6 for EP Patent No. 2219647, dated Sep. 24, 2014, 20 pages.
Interlocutory Decision in Opposition proceedings, in EP Application No. 08850935.1, dated May 16, 2014, 75 pages.
Letter from Richard Bassett, Potter Clarkson LLP, to the European Patent Office dated Jan. 24, 2014, regarding European Patent No. EP2219647, 13 pages.
Letter to the European Patent Office from Dr. M. Best, Lederer & Keller, dated Jan. 24, 2014, in preparation of the oral proceedings scheduled for May 26, 2014 regarding European Patent No. 2219647, 11 pages.
Opposition reference European Application Patent No. EP 2219647, dated.
Opposition to European Patent No. 2 219 647 (H. Lundbeck A/S and Takeda Pharmaceuticals U.S.A. Ltd). by Sandoz AG, dated Jul. 2, 2013, 30 pages.
Reply to Patentee's Grounds of Appeal in EP Application No. 08850935.1, dated Feb. 27, 2015, 27 pages.
Response filed by Richard S. Bassett, Potter Clarkson LLP on Feb. 20, 2015 to the Notification, Ground of Appeal dated Oct. 20, 2014 to the European Patent Office for European Patent No. EP2219647, 9 pages.
Response to the Grounds of Appeal filed by Opponent in European Patent No. 2 219 647, dated Jun. 5, 2015, 4 pages.
Statement of Arguments by the Opponent in IL Patent Application No. 20546, dated Jan. 29, 2015, 13 pages.
Statement On a Nonproprietary Name Adopted by The USAN Counsil RE EP 08 850 935, Printed Sep. 28, 2012.
Submission of Letter to The European Patent Office dated Jan. 24, 2014, from Richard Bassett, Potter Clarkson LLP, response to the communication under Rule 115(1) EPC dated Oct. 28, 2013, 13 pages.

(Continued)

Primary Examiner — Rei Tsang Shiao
(74) Attorney, Agent, or Firm — Fish & Richardson P.C.

(57) ABSTRACT

New pharmaceutical uses of 1-[2-(2,4-dimethylphenylsulfanyl)phenyl]piperazine and pharmaceutically acceptable salts thereof are provided.

9 Claims, 13 Drawing Sheets

(56) References Cited

OTHER PUBLICATIONS

Figure 1:
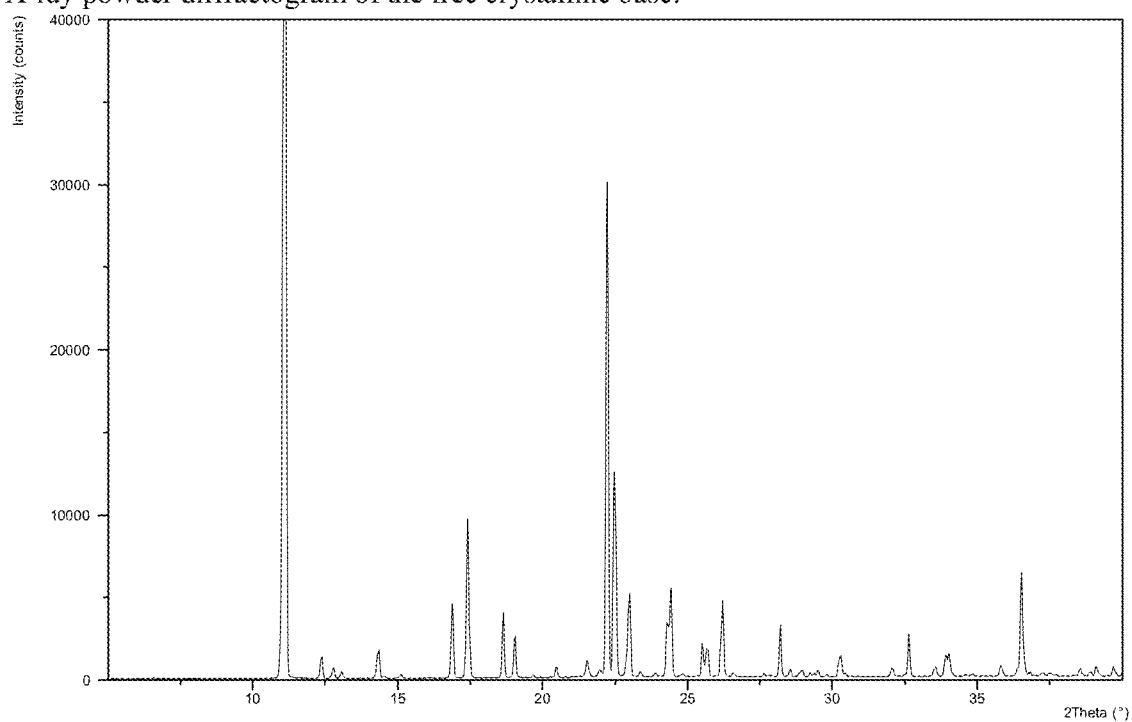

Submission re Appeal in EP Patent No. 2219647, dated Sep. 26, 2014, 15 pages.
Summons dated Oct. 28, 2013 to Attend Oral Proceedings in European Patent No. 2 219 647, 10 pages.
'GPnotebook,' [online]. "ICD-10 depression diagnostic criteria," retrieved on Mar. 25, 2014. Retrieved from the Internet: http://www.gpnotebook.co.uk/simplepage.cfm?ID=x20091123152205182440, 1 page.
"Clinical Study Results for vortioxetine, a novel investigational multimodal antidepressant," NCDEU Annual Meeting; May 31, 2013, Hollywood, Florida, USA, 2 pages.
Alvarez, et al., A double-blind, randomized, placebo-controlled, active reference study of Lu AA21004 in patients with major depressive disorder, The International Journal of Neuropsychopharmacology, 2012, 15:589-600.
Anagnostaras et al., "Hippocampus and Contextual Fear Conditioning: Recent Controversies and Advances," Hippocampus, vol. 11, No. 1, pp. 8-17 (2001).
Anagnostaras et al., "Temporally Graded Retrograde Amnesia of Contextual Fear after Hippocampal Damage in Rats: Within-Subjects Examination", The Journal of Neuroscience, vole 19, No. 3, pp. 1106-1114 (1999).
Anderson, et al., Evidence-based guidelines for treating depressive disorders with antidepressants: A revision of the 2000 British Association for Psychopharmacology guidelines, Journal of Psychopharmacology, 2008, 22: 343-396.
Antai-Otong, D.; Perspect. Psychiatr. C.; vol. 49(1); pp. 29 (2004).
Anttila and Leinonen, "New Drugs: A Review of the Pharmacological and Clinical Profile of Mirtazapine," CNS Drug Reviews, 7(3):249-264 (2001).
Ashton, et al., Reversal of Fluoxetine-Induced Sexual Dysfunction by Switching to Escitalopram, Journal of Sex & Marital Therapy, 2004, 30:1-2.
Assessment Report for Brintellix to Committee for Medicinal Products for Human Use (CHMP), Oct. 24, 2013, 159 pages.
Baldwin, et al., A randomised, double-blind, placebo controlled, duloxetine-referenced, fixed-dose study of three dosages of Lu AA21004 in acute treatment of major depressive disorder (MDD), European Neuropsychopharmacology, 2012, 22: 482-491.
Baldwin,, et al., Symptoms of Fatigue and Sleepiness in Major Depressive Disorder, J Clin Psychiatry 2006, 67 (suppl 6).
Baron, Detection Of Neuropathic Pain Syndromes, Dtsch Arztebl, 2006, 103: 2720-30.
Buoen et al., "How First-Time-in-Human Studies are Being Performed: A Survey of Phase I Dose-Escalation Trials in Healthy Volunteers Published Between 1995 and 2004," J Clin. Pharmacol., 45:1123-1136 (2005).
Chan et al., "Duloxetine pharmacokinetics are similar in Japanese and Caucasian subjects," Br J Clin Pharmacol., 63:310-314 (2006).
Chung et al., "Clozapine increases both acetylcholine and dopamine release iin rat ventral hippocampus: role of 5-HT 1A receptor agonism", Brain Research, vol. 1023, pp. 54-63 (2004).
Correll, Vortioxetine: A New Antidepressant Choice in the United States, Oct. 2, 2013, http://www.medscape.com/viewarticle/811959, pp. 1-5.
Curriculum Vitae for Dr. Parmentier, Jun. 6, 2013, 12 pages.
Curriculum Vitae for Professor Volz, Apr. 24, 2013, 2 pages.
DeBattista et al., "A Placebo-Controlled, Randomized, Double-Bline Study of Adjunctive Bupropion Sustained Release in the Treatment of SSRI-Induced Sexual Dysfunction", J. Clin. Psychiatry, vol. 66, No. 7, pp. 844-848 (2005).
DeBattista, et al., Serotonergic Synergism: The Risks and Benefits of Combining the Selective Serotonin Reuptake Inhibitors with Other Serotonergic Drugs, Biol Psychiatry, 1998, 44:341-347.
Declaration of Dr. Henk Parmentier, Jun. 6, 2013, 3 pages.
Declaration of Professor Hans-Peter Volz, Apr. 24, 2013, 3 pages.
Dharmshaktu, et al., Efficacy of Antidepressants as Analgesics: A Review, J Clin Pharmacol, 2012, 52:6-17.
Eder et al., "Association of Olanzapine-Induced Weight Gain with an Increase in Body Fat", Am J Psychiatry, vol. 158, No. 10, pp. 1719-1722 (2001).
Fairweather et al., "A double blind comparison of the effects of fluoxetine and amitriptyliine on cognitive function in elderly depressed patients", Human Psychopharmacology, vol. 8, pp. 41-47 (1993).
Fanselow et al. "Contional and Unconditional Components of Post-Shock Freezing", Biol. Sci., vol. 15, No. 4, pp. 177-182 (1980).
Fava, et al., Treatment of recurrent depression, Expert Rev. Neurotherapeutics, 2006, 6:1735.
Fava, M. and Rankin, M.; J. Clin. Psychiatry; 63(suppl 5); 13 (2002).
FDA Approval labeling for PROZAC® Fluoxetine Capsules, USP, Fluoxetine Oral Solution, USP, pp. 1-35, action date Sep. 20, 2006.
FDA Approval labeling for ZOLOFT® (sertraline hydrochloride) Tablets and Oral Concentrate, pp. 1-43, action date Sep. 14, 2006.
FDA label for Cymbalta® (duloxetine): action date Sep. 20, 2006, 29 pages.
FDA label for Lexapro® (escitalopram): action date Aug. 29, 2002, 24 pages.
GLG News; "Lundbeck's 'Serotonin Modulator and Stimulator' Lu AA21004: How Novel? How Good?"; Oct. 16, 2007.
Gould, "Salt Selection for basic drugs," Int'l J Pharma., 1986, 33:201-217.
Gregorian et al., "Antidepressant-Induced Sexual Dysfunction," Ann Pharmacother., Oct. 2002, 36:1577-1589.
Guidelines for Phase I Clinical Trials; The Association of the British Pharmaceutical Industry; London, 2007 Edition, 49 pages.
Harvey et al., "Clinical Implications of Antidepressant Drug Effects on Sexual Function," Ann Clin Psychiatry, 1995, 7(4):189-201.
Iyengar et al., "Efficacy of Duloxetine, a Potent and Balanced Serotonin-Norepinephrine Reuptake Inhibitor in Persistent Pain Models in Rats," J Pharmacol Exp Ther., 311(2):576 (2004).
Jacobsen, Paula et al., Poster presented at the 29th CINP World Congress of Neuropsychopharmacology, Jun. 22 to 26, 2014, Vancouver, Canada, 12 pages.
Katona et al., "A randomized, double-blind, placebo-controlled, duloxetine-referenced, fixed-dose study comparing the efficacy and safety of Lu AA21004 in elderly patients with major depressive disorder," Int. Clin. Psychopharm., 27:215-223 (2012).
Khawam, et al., Side effects of antidepressants: An overview, Cleveland Clinic Journal of Medicine, 2006, 73:351-361.
Lam, "Sleep disturbances and depression: a challenge for antidepressants", International Clinical Psychopharmacology, vol. 21 (suppl 1), S25-S29 (2006).
Larsen Kari, "Lundbeck says antidepressant LuAA21004 positive in Phase II—shares jump", Internet article, http://health.apmnews.com/depechesPub1 (2007).
Levkovitz et al., "The SSRIs drag Fluoxetine, but not the noradrenergic tricyclic drug Desipramine, improves memory performance during acute major depression", Brain Research Bulletin, vol. 58, No. 4, pp. 345-350 (2002).
Margolese and Assalian, "Sexual Side Effects of Antidepressants: A Review," J Sex & Marital Therapy, Fall 1996, 22(3):209-217.
Mayers et al., "Antidepressants and their effect on sleep", Human Psychopharmacology, Hum Psychopharmacol Clin Exp, vol. 20, pp. 533-559 (2005).
Mealy et al., "Lu-31-130/Lu-AA-21004/Lu-35-138" Drugs of the Future 200409 ES, vol. 20, No. 9; Sep. 2004; pp. 954-955.
Molzen, et al., Serotonin Reuptake Inhibitors: The Corner Stone in Treatment of Depression for Half a Century—A Medicinal Chemistry Survey, Current Topics in Medicinal Chemistry, 2006, 6: 1801.
Paradiso et al., "Cognitive Impairment in the Euthymic Phase of Chronic Unipolar Depression", vol. 185, No. 12, pp. 748-754 (1997).
Phillips et al., "Differential Contribution of Amygdala and Hippocampus to Cued and Contextual Fear Conditioning", Behavioral Neuroscience, vol. 106, No. 2, pp. 274-285 (1992).
Posner, "Chapter 4, Exploratory Development," in "The Textbook of Pharmaceutical Medicine, 5th Edition," ed. Griffin and O'Grady, Blackwell Publishing Ltd: Oxford, UK, Chapter 4, 144-161 (2006).
Preskorn, S. H. et al.; Antidepressants: Past, Present and Future; Springer, Berlin; vol. 157; pp. 250-252 (2004).

(56) References Cited

OTHER PUBLICATIONS

Preston, Recent Advances in the treatment of Neurodegenerative disorders and cognitive function, (eds), Racagni and Langer, Basel Karger, pp. 89-93 (1994).

Raskin et al., Efficacy of Duloxetine on Cognition, Depression, and Pain in Elderly Patients With Major Depressive Disorder: An 8-Week, Double-Blin, Placebo-Controlled Trial, Am J. Psychiatry 164, Jun. 6, 2007, pp. 900-909.

Ravnkilde et al., "Cognitive deficits in major depression", Scandinavian Journal of Psychology, vol. 43, pp. 239-251 (2002).

Rothschild, "New Directions in the Treatment of Antidepressant-Induced Sexual Dysfunction," Clin. Ther., 22(suppl A):A42-A61 (2000).

Ruhe, et al., Switching Antidepressants After a First Selective Serotonin Reuptake Inhibitor in Major Depressive Disorder: A Systematic Review, J Clin Psychiatry 2006, 67:1836.

Serajuddin, "Salt formation to improve drag solubility," Adv Drag Delivery Rev., 2007, 59:603-616.

Serretti, et al., "Treatment-Emergent Sexual Dysfunction Related to Antidepressants, A Meta-Analysis," J Clin Psychopharmacol., Jun. 2009, pp. 29(3):259-266.

Sharma et al., "Pharmacokinetics and Safety of Duloxetine, a Dual-Serotonin and Norepinephrine Reuptake Inhibitor," J Clin Pharmacol., 40:161-167 (2000).

Sogaard et al., "The Pharmacokinetics of Escitalopram after Oral and Intravenous Administration of Single and Multiple Doses to Healthy Subjects," J Clin Pharmacol., 45:1400-140 (2005).

Sokolski et al., "Once-daily high-dose pindolol for SSRI-refractory depression", Psychiatry Research, vol. 125, pp. 81-86 (2004).

Spinks, et al., Serotonin Reuptake Inhibition: An Update on Current Research Strategies, Current Medicinal Chemistry, 2002, 9:799-810.

Stahl, Selectivity of SSRIs: individualising patient care through rational treatment choices, International journal of Psychiatry in Clinical Practice, 2004, 8: 3-10.

Sumiyoshi et al., "Enhancement of cognitive performance in schizophrenia by addition of tandospirone to neuroleptic treatment," Am J Psychiatry, 2001, 158(10):1722-1725.

Taylor, D.T. et al.; The Maudsley: Prescribing Guidelines; Informa Healthcare; London, 9th Edition, pp. 231-234 (2007).

Thase, "US Food and Drug Administration's Review of the Novel Antidepressant Vortioxetine," J Clin Psychiatry, Jan. 2015, 76:1, 9 pages.

TIMA (Texas Implementation of Medication Algorithms) Guideline for Treating Major Depressive Disorder 2000, 91 pages.

To, et al., Treatment of depression in primary care—Part 2: Principles of maintenance treatment, BCMJ, 2002, 44: 79-484 Articles.

Vissers et al., "Pharmacological correlation between the formalin test and the neuropathic pain behavior in different species with chronic constriction injury," Pharmacol Biochem Behavior, 84:479-486 (2006).

Westenberg, et al., Tolerability and safety of fluvoxamine and other antidepressants, IntJ Clin Pract, 2006, 60: 482-491.

Wilson et al., "Antidepressants and Sleep. A Qualitative Review of the Literature", Drugs 2005; 65(7); pp. 927-947.

Wilson et al., "Using sleep to evaluate comparative serotonergic effects of paroxetine and citalopram", European Neuropsychopharmocology, 14, 2004, pp. 367-372.

Worthington, et al., Treatment of Antidepressant-Induced Sexual Dysfunction, Drugs of Today, 2003, 39:887-896.

* cited by examiner

X-ray powder diffractogram of the free crystalline base:

X-ray powder diffractogram of the beta form of the hydrobromide

THERAPEUTIC USES OF COMPOUNDS HAVING COMBINED SERT, 5-HT3 AND 5-HT1A ACTIVITY

CROSS REFERENCE TO PRIOR APPLICATIONS

This is a continuation of U.S. application Ser. No. 15/661,392, filed Jul. 27, 2017, which is a continuation of U.S. application Ser. No. 15/043,167, filed Feb. 12, 2016, now U.S. Pat. No. 9,744,166, which is a continuation of U.S. application Ser. No. 12/741,780, filed Oct. 6, 2010, now U.S. Pat. No. 9,278,096, which is a U.S. National Phase application under 35 U.S.C. § 371 of International Patent Application No. PCT/DK2008/050271, filed Nov. 12, 2008, which claims the priority of Danish Patent Application No. PA 200701607, filed Nov. 13, 2007; U.S. Provisional Application No. 60/987,710, filed Nov. 13, 2007; Danish Patent Application No. PA 200701788, filed Dec. 14, 2007; U.S. Provisional Application No. 61/013,722, filed Dec. 14, 2007; Danish Patent Application No. PA 200801300, filed Sep. 17, 2008; and U.S. Provisional Application No. 61/097,840, filed Sep. 17, 2008. The entire content of each of the aforementioned applications is hereby incorporated herein by reference in its entirety. The aforementioned International Application published in English on May 22, 2009 as WO 2009/062517 under PCT Article 21(2).

FIELD OF THE INVENTION

The present invention relates to the therapeutic use of compounds which have a combined SERT, $5\text{-}HT_3$ and $5\text{-}HT_{1A}$ activity.

BACKGROUND OF THE INVENTION

Selective serotonin reuptake inhibitors (SSRI) have for years been favoured by physicians for the treatment of many CNS diseases, such as depression and anxiety because the are effective and have a safety profile which is favourable compared to the previous generation of CNS drugs, i.e. the so-called tri-cyclics. Nevertheless, SSRI's are also hampered by a significant fraction of non-responders, i.e. patients who do not or who do not fully respond to the treatment. Moreover, typically an SSRI does not begin to show an effect until after weeks of treatment. Finally, although SSRI's typically give rise to less adverse effects than tri-cyclics, the administration of SSRI's often brings about adverse effects, such as sexual side effects and sleep problems. These adverse effects are difficult to live with for many patients and cause treatment drop outs for a significant fraction of patients receiving SSRI's.

It is known that a combination of inhibition of the serotonin transporter (SERT) with an activity on one or more serotonin receptors may be beneficial. It has been reported that the combination of pindolol, which is a $5\text{-}HT_{1A}$ partial agonist, with a serotonin reuptake inhibitor gives rise to fast onset of effect [Psych. Res., 125, 81-86, 2004]. This would imply a shorter onset of the effect of increased serotonin levels in the clinic and an augmentation or potentiation of the therapeutic effect of the serotonin reuptake inhibitor.

CNS related diseases, such as e.g. depression, anxiety and schizophrenia are often co-morbid with other disorders or dysfunctionalities, such as cognitive deficits or impairment [Scand.J.Psych., 43, 239-251, 2002; Am.J.Psych., 158, 1722-1725, 2001].

Several neurotransmitters are presumed to be involved in the neuronal events regulating cognition. In particular, the cholinergic system plays a prominent role in cognition, and compounds affecting the cholinergic system are thus potentially useful for the treatment of cognitive impairment. Compounds affecting the $5\text{-}HT_{1A}$ receptor and/or the $5\text{-}HT_3$ receptor are known to affect the cholinergic system, and they may as such be useful in the treatment of cognitive impairment.

Hence, a compound exerting $5\text{-}HT_{1A}$ and/or $5\text{-}HT_3$ receptor activity would be expected to be useful in the treatment of cognitive impairment. A compound which moreover also exerts SERT activity would be particularly useful for the treatment of cognitive impairment in patients who are also suffering from a disease which will benefit from a (faster) increase in the serotonin levels.

The international application published as WO 03/029232 discloses a range of compounds including 1-[2-(2,4-dimethylphenylsulfanyl)phenyl]piperazine (example 1e) having serotonin reuptake inhibiting activity.

The international application WO 2007/144005 which has published after the priority date of the present application discloses that 1-[2-(2,4-dimethylphenylsulfanyl)-phenyl]piperazine is also a $5\text{-}HT_3$ antagonists and a $5\text{-}HT_{1A}$ partial agonist.

SUMMARY OF THE INVENTION

The present inventors have surprisingly found that 1-[2-(2,4-dimethylphenylsulfanyl)-phenyl]piperazine exerts a combination of SERT inhibition, $5\text{-}HT_3$ antagonism and $5\text{-}HT_{1A}$ agonism. Accordingly, the invention provides a method for the treatment of diseases, the method comprising the administration of a therapeutically effective amount of 1-[2-(2,4-dimethylphenylsulfanyl)phenyl]-piperazine or a pharmaceutically acceptable salt thereof to a patient in need thereof.

In one embodiment, the invention relates to the use of 1-[2-(2,4-dimethylphenylsulfanyl)phenyl]piperazine or a pharmaceutically acceptable salt thereof in the manufacture of a medicament for the treatment of diseases.

In one embodiment, the invention provides 1-[2-(2,4-dimethylphenylsulfanyl)-phenyl]piperazine or a pharmaceutically acceptable salt thereof for use in the treatment of diseases.

FIGURES

FIG. 1: XRPD of crystalline base

Figure 2:
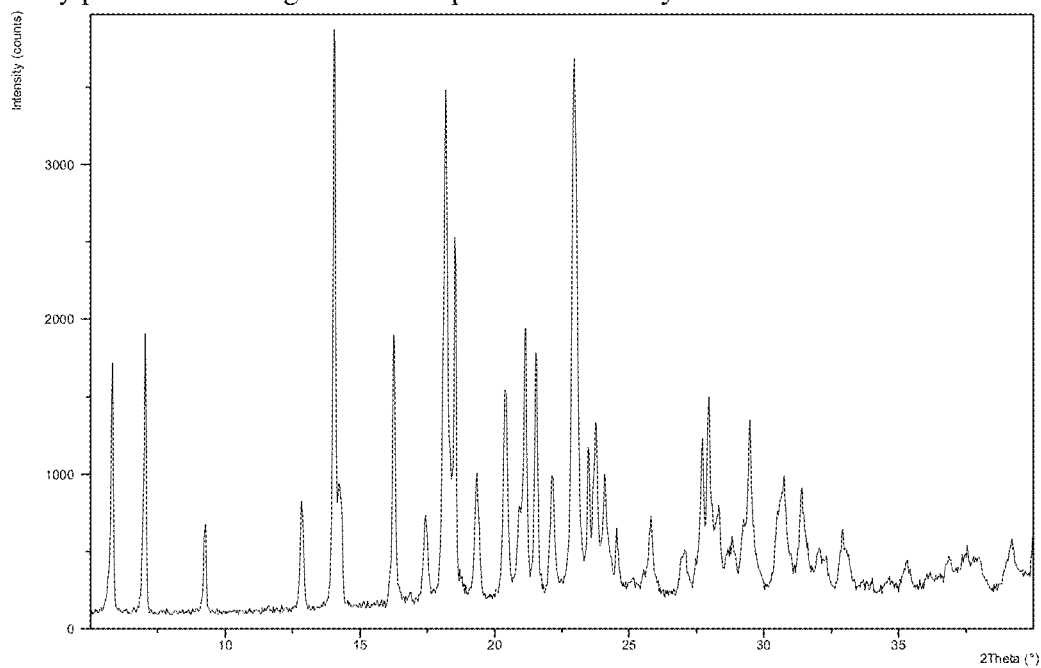

FIG. 2: XRPD of alpha form of hydrobromide salt

Figure 3:
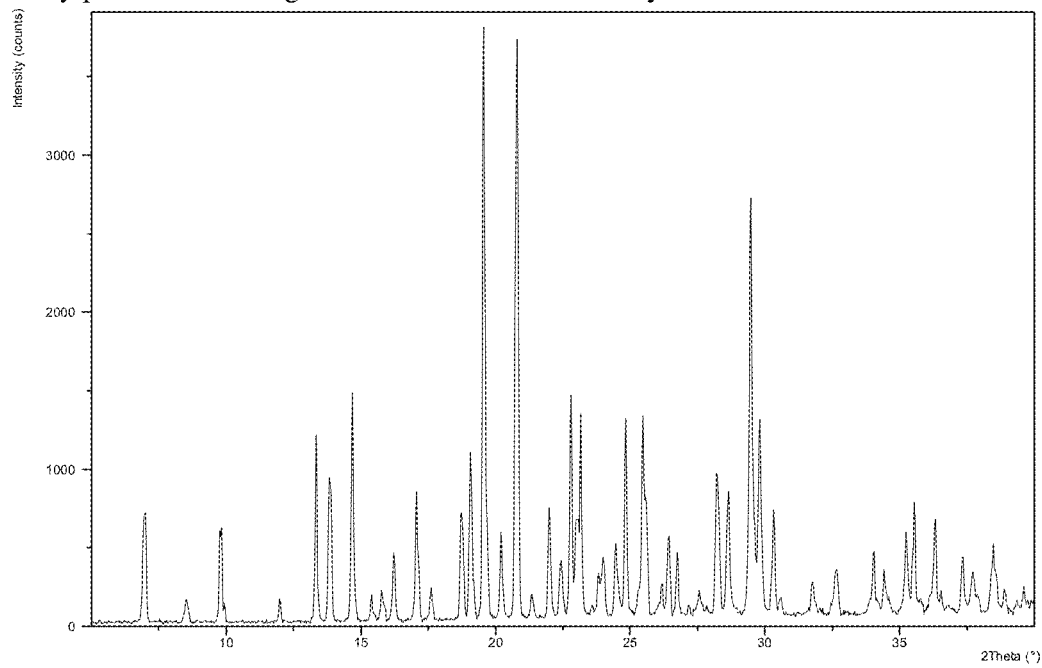

FIG. 3: XRPD of beta form of hydrobromide salt

Figure 4:
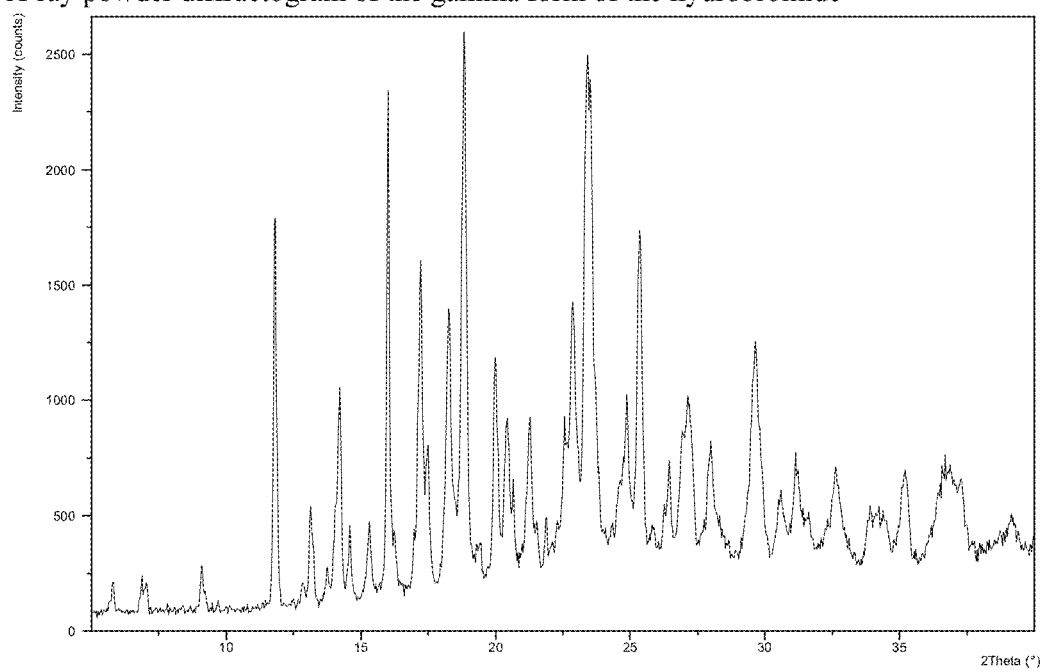

FIG. 4: XRPD of gamma form of hydrobromide salt

Figure 5:
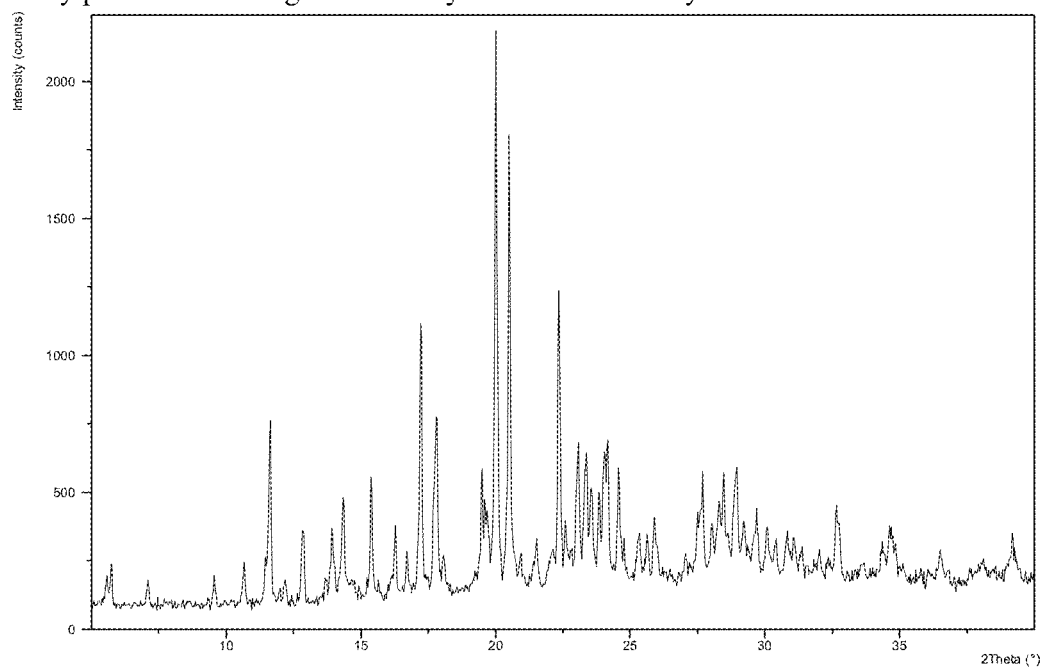

FIG. 5: XRPD of hemi hydrate of hydrobromide salt

Figure 6:
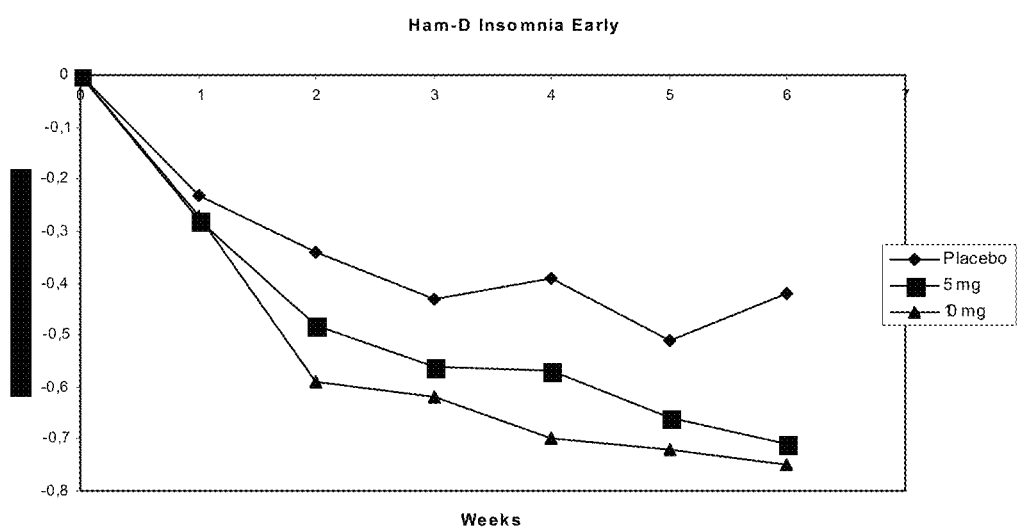
Figure 7:
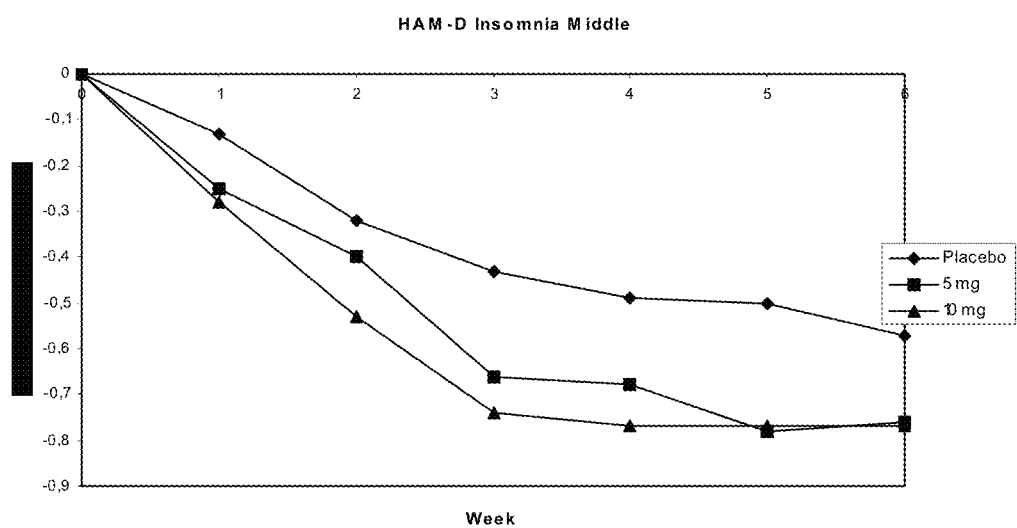
Figure 8:
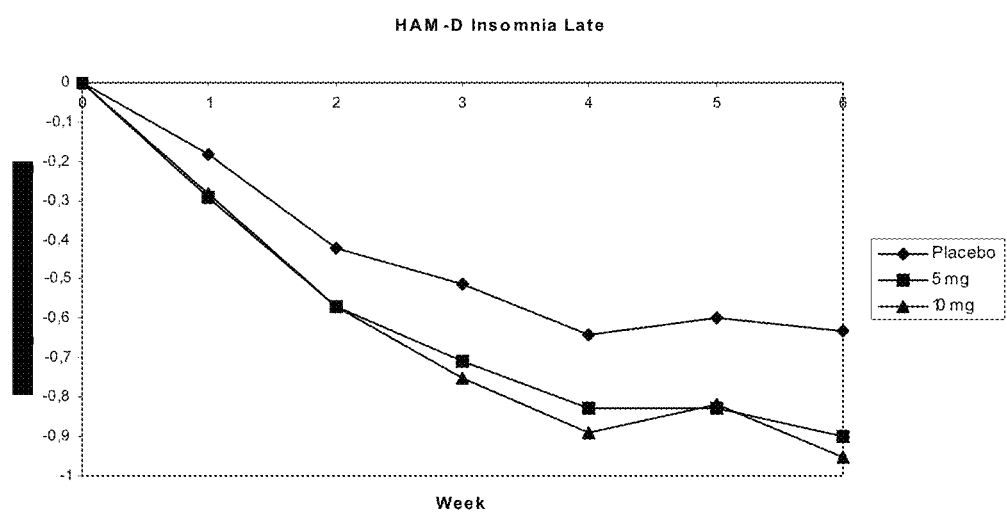
Figure 9A:
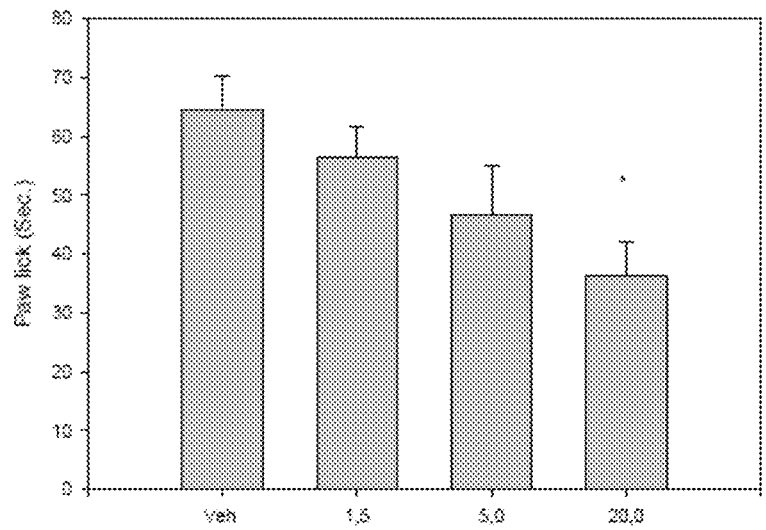

FIG. 6: Change in the HAM-D rating item 4 (Insomnia Early) for placebo, 5 mg and 10 mg compound I (HBr salt) over 6 weeks. There were approximately 100 patients in each group FIG. 7: Change in the HAM-D rating item 5 (Insomnia Middle) for placebo, 5 mg and 10 mg compound I (HBr salt) over 6 weeks. There were approximately 100 patients in each group FIG. 8: Change in the HAM-D rating item 6 (Insomnia Late) for placebo, 5 mg and 10 mg compound I (HBr salt) over 6 weeks. There were approximately 100 patients in each group FIG. 9a: Effect of compound I in the intradermal formalin test in the 0-5 minutes period. X-axis shows the amount of compound administered; Y-axis shows the amount of time (sec) spent licking the paw.

Figure 9B:
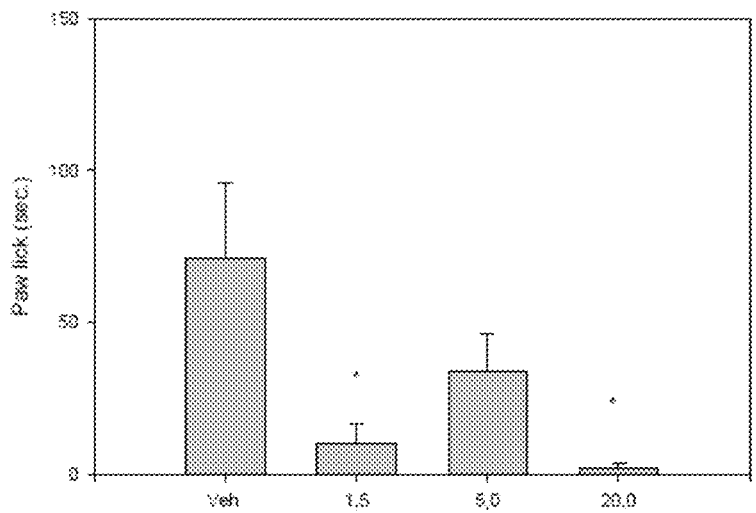

FIG. 9b: Effect of compound I in the intradermal formalin test in the 20-30 minutes period. X-axis shows the amount of compound administered; Y-axis shows the amount of time (sec) spent licking the paw.

Figure 10A:
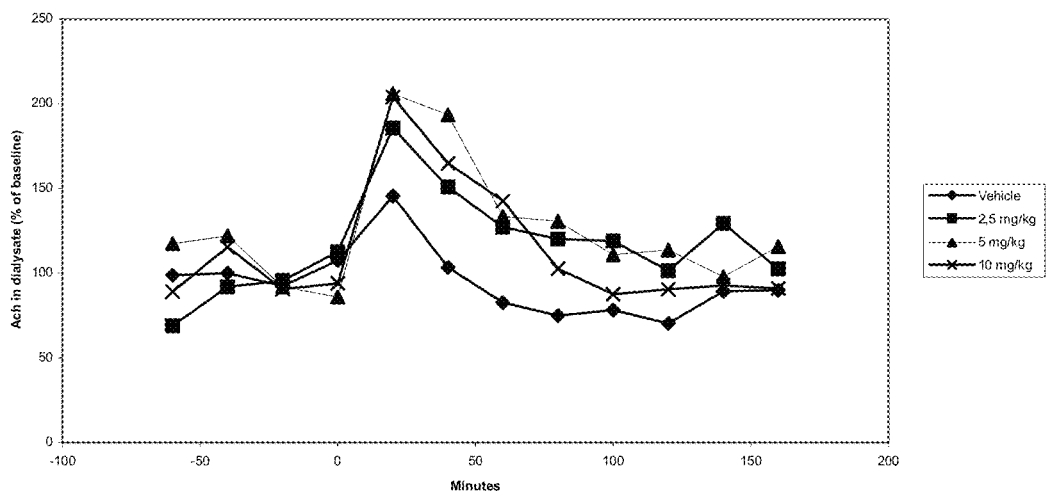

FIG. 10a: Extra-cellular acetylcholine levels in prefrontal cortex in freely moving rats upon administration of 1-[2-(2,4-dimethylphenylsulfanyl)phenyl]piperazine HBr salt.

Figure 10B:
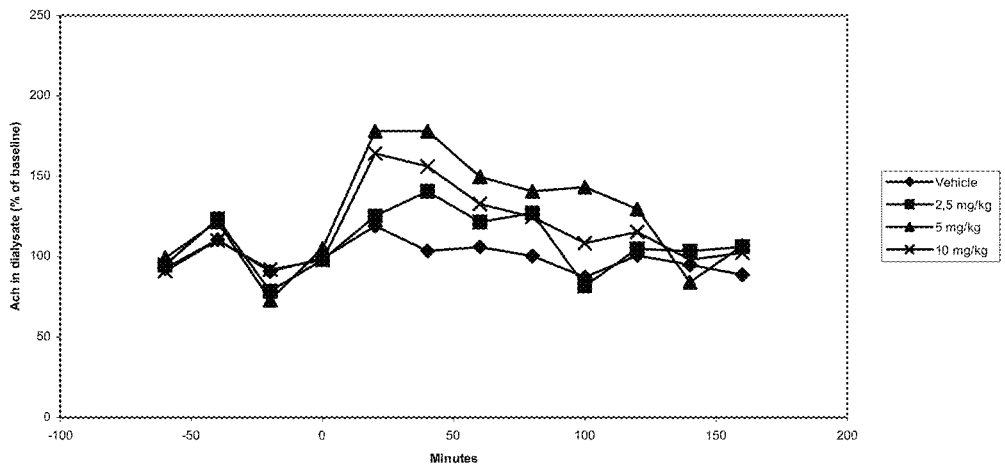

FIG. 10b: Extra-cellular acetylcholine levels in ventral hippocampus in freely moving rats upon administration of 1-[2-(2,4-dimethylphenylsulfanyl)phenyl]piperazine HBr salt.

Figure 11:
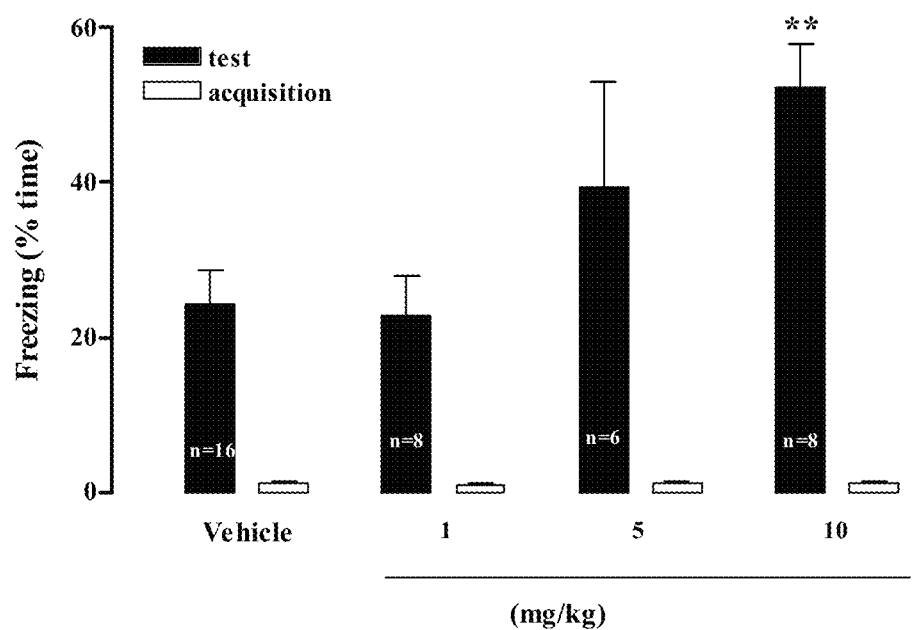

FIG. 11: Effect of 1-[2-(2,4-dimethylphenylsulfanyl)phenyl]piperazine HBr salt on contextual fear conditioning in Sprague-Dawley rats when given 60 minutes before acquisition. Freezing behaviour was scored during 58-s habituation period prior to the foot shock US (pre-shock acquisition) (white bars). Freezing behaviour was measured 24 h after the training (retention test) (black bars).

Figure 12:
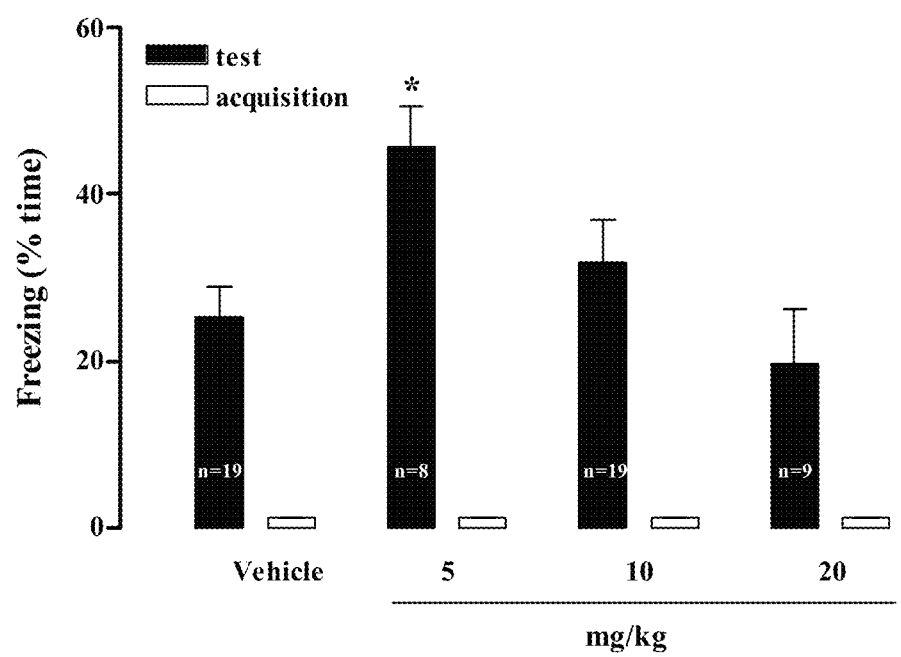

FIG. 12: Effect of 1-[2-(2,4-dimethylphenylsulfanyl)phenyl]piperazine HBr salt on contextual fear conditioning in Sprague-Dawley rats when given 1 h prior to the retention test. Freezing behaviour was scored during 58-s, prior to the foot shock US (acquisition) (white bars). Freezing behaviour was measured 24 h after the training (retention test) (black bars).

Figure 13:
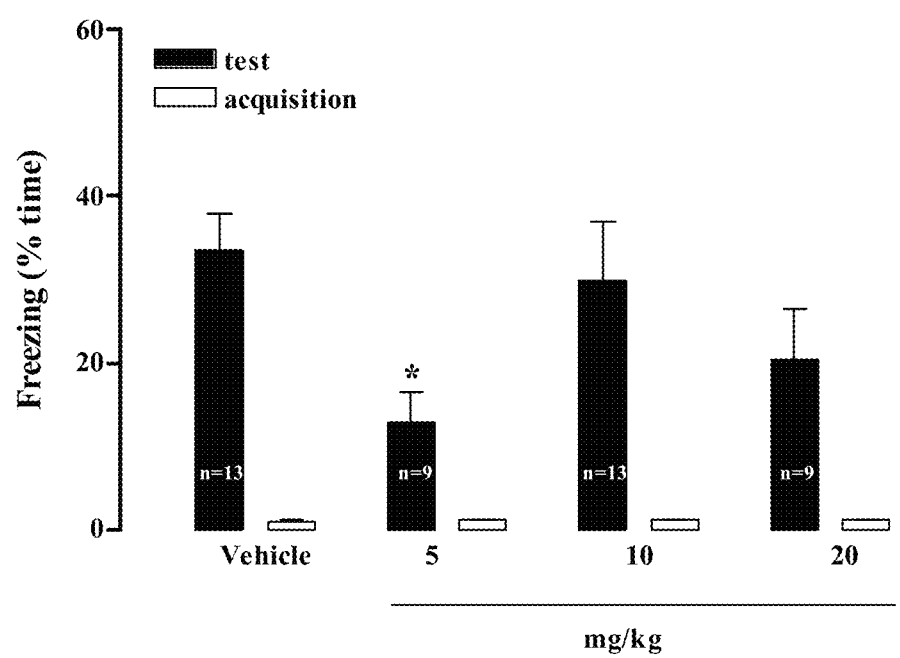

FIG. 13: Effect of 1-[2-(2,4-dimethylphenylsulfanyl)phenyl]piperazine HBr salt on contextual fear conditioning in Sprague-Dawley rats when given immediately after the acquisition. Freezing behaviour was scored during 58-s, prior to the foot shock US (pre-sock acquisition) (white bars). Freezing behaviour was measured 24 h after the training (retention test) (black bars).

DETAILED DESCRIPTION OF THE INVENTION

The invention relates to the use of compound I, i.e., 1-[2-(2,4-dimethylphenyl-sulfanyl)-phenyl]piperazine, the structure of which is

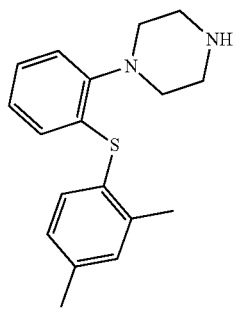 [SMILES: Cc1ccc(Sc2ccccc2N2CCNCC2)c(C)c1]

and pharmaceutically acceptable salts thereof.

In one embodiment, said pharmaceutically acceptable salts are acid addition salts of acids that are non-toxic. Said salts include salts made from organic acids, such as maleic, fumaric, benzoic, ascorbic, succinic, oxalic, bis-methylene-salicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, theophylline acetic acids, as well as the 8-halotheophyllines, for example 8-bromotheophylline. Said salts may also be made from inorganic salts, such as hydrochloric, hydrobromic, sulfuric, sulfamic, phosphoric and nitric acids. Particular mentioning is made of salts made from methanesulfonic acid, maleic acid, fumaric acid, meso-tartaric acid, (+)-tartaric acid, (−)-tartaric acid, hydrochloric acid, hydrobromic acid, sulphuric acid, phosphorous acid and nitric acid. Distinct mentioning is made of the hydrobromide salt.

In one embodiment, the invention relates to the use of compound I as disclosed provided said compound is not the free base of 1-[2-(2,4-dimethylphenylsulfanyl)-phenyl]piperazine in a non-crystalline form.

Oral dosage forms, and in particular tablets, are often preferred by the patients and the medical practitioner due to the ease of administration and the consequent better compliance. For tablets, it is preferable that the active ingredients are crystalline. In one embodiment, the invention relates to the use of compounds that are crystalline. The crystallinity of compounds used in the present invention is evidenced by the XRDP shown in FIGS. 1-5. WO 2007/144005 discloses XRPD reflections of further salts used in the present invention. The table below summarises the major XRDP reflections of some compounds used in the present invention.

| Selected X-ray peak positions (°2θ), All values ±0.1° | | | | |
|---|---|---|---|---|
| Crystalline base | 11.10 | 16.88 | 17.42 | 22.23 |
| hydrobromide (α) | 5.85 | 9.30 | 17.49 | 18.58 |
| hydrobromide (β) | 6.89 | 9.73 | 13.78 | 14.62 |
| hydrobromide (γ) | 11.82 | 16.01 | 17.22 | 18.84 |
| hydrobromide (hydrate) | 10.69 | 11.66 | 15.40 | 17.86 |

In one embodiment, the crystals used in the present invention are solvates, i.e. crystals wherein solvent molecules form part of the crystal structure. The solvate may be formed from water, in which case the solvates are often referred to as hydrates. Alternatively, the solvates may be formed from other solvents, such as e.g., ethanol, acetone, or ethyl acetate. The exact amount of solvate often depends on the conditions. For instance, hydrates will typically loose water as the temperature is increased or as the relative humidity is decreased.

In one embodiment, the compounds of the present invention are unsolvated crystals.

Some compounds are hygroscopic, i.e., they absorb water when exposed to humidity. Hygroscopicity is generally regarded as an undesired property for compounds that are to be presented in a pharmaceutical formulation, in particular in a dry formulation, such as tablets. In one embodiment, the invention provides crystals with low hygroscopicity. For oral dosage forms using crystalline active ingredients it is also beneficial if said crystals are well-defined. In the present context, the term "well-defined" in particular means that the stoichiometry is well-defined, i.e., that the ratio between the ions forming the salt is the ratio between small integers, such as 1:1, 1:2, 2:1, 1:1:1, etc. In one embodiment, the compounds of the present invention are well-defined crystals.

The crystalline compounds used in the present invention may exist in more than one form, i.e., they may exist in polymorphic forms. Polymorphic forms exist if a compound can crystallize in more than one form. The present invention is intended to encompass all such polymorphic forms, either as pure compounds or as mixtures thereof.

In one embodiment, the present invention uses compounds in a purified form. The term "purified form" is intended to indicate that the compound is essentially free of other compounds or other forms of the same compound, as the case may be.

As evidenced, e.g., by FIGS. 2-5, compounds used in the present invention, in casu the hydrobromide salt, may exist in several forms, i.e., be polymorphic. The polymorphic forms have different properties, and as shown in example 2. The beta form of the hydrobromide salt is the more stable as demonstrated by the higher DSC melting point and the lower solubility. Moreover, the beta form has an attractive combination of low hygroscopicity and solubility, which makes this compound particular suited for making tablets. Hence, in one embodiment, the invention provides the use of the hydrobromide salt of 1-[2-(2,4-dimethylphenylsulphanyl)-phenyl]piperazine with XRDP reflections at approximately 6.89, 9.73, 13.78 and 14.62 (° 2θ), and in particular with an XRPD as shown in FIG. 3.

The solubility of an active ingredient is also of significance for the choice of dosage form as it may have a direct impact on bio-availability. For oral dosage forms, a higher solubility of the active ingredient is generally believed to be beneficial as it increases the bio-availability.

As shown in example 1, the compounds used in the present invention are potent inhibitors of the human serotonin transporter, i.e., they inhibit serotonin reuptake. Moreover, the compounds are potent antagonists at the mouse, rat, guinea pig and canine 5-HT$_3$ receptor. At the human 5-HT$_3$ receptor, cloned into oocytes, the compounds were found to be antagonists at low concentrations (IC$_{50}$ approx. 20 nM), whilst at higher concentrations the compounds display agonistic properties (ED$_{50}$=2.1 μM). A subsequent application of compounds of the present invention at high concentration did not show any agonistic response, which could be due to rapid desensitization or direct antagonism in vitro. Thus, at low concentrations compounds of the present invention display a marked antagonism at the human 5-HT$_3$ receptor as observed on the 5-HT$_3$ receptor from other species. The data also shows that the compounds used in the present invention are agonists at the 5-HT$_{1A}$ receptor with a K$_i$ value of 15 nM and 96% intrinsic activity (or efficacy). WO 2007/144005 discloses slightly different values. It is, however, believed that this difference is a matter of degree and that it does not call for a fundamental change in the perception of the compound.

As mentioned above, there is theoretical reasons for why compounds that are 5-HT$_{1A}$ agonists and/or 5-HT$_3$ antagonists are expected to be useful in the treatment of cognitive deficits, and this is supported by clinical evidence. T. Sumiyoshi in *Am.J.Psych.*, 158, 1722-1725, 2001 reports a study wherein patients received typical anti-psychotics, such as haloperidol, sulpride and pimozide, which all lack 5-HT$_{1A}$ activity in combination with placebo or tandospirone, which is a 5-HT$_{1A}$ agonist. Patients receiving tandospirone on top of the anti-psychotic showed an improvement in their cognitive performance whereas patients receiving placebo did not. Similarly, atypical anti-psychotics, such as clozapine, which are also 5-HT$_{1A}$ agonists enhance cognition in schizophrenic patients, whereas typical anti-psychotics, such as haloperidol which have no 5-HT$_{1A}$ activity, do not, [Y. Chung, *Brain Res.*, 1023, 54-63, 2004]. In a randomised double blind crossover study in healthy male subjects, assessments of verbal and spatial memory and sustained attention demonstrated that the 5-HT$_3$ antagonist, alosetron attenuated scopolamine induced deficits in verbal and spatial memory [Preston, *Recent Advances in the treatment of Neurodegenerative disorders and cognitive function*, 1994, (eds.) Racagni and Langer, Basel Karger, p. 89-93].

As shown in example 5, the compounds of the present invention give rise to an increase in the extra-cellular level of acetylcholine in the prefrontal cortex and the ventral hippocampus in rats. These pre-clinical findings are expected to translate into a clinical effect in the treatment of cognitive impairments, cf. the use of acetylcholine esterase inhibitors in the treatment of cognitive impairments, e.g., in Alzheimer's disease. Further support to this position can be found in example 6, wherein data show that compounds of the present invention enhance contextual memory in rats. All in all, the pharmacological profile of the compounds of the present invention combined with the effects on acetylcholine levels and memory in rats strongly suggest that the compounds used in the present invention are useful in the treatment of cognitive impairment or the treatment of diseases wherein the patient also suffers from cognitive impairment.

Cognitive impairment is among the classic features of depression, such as major depressive disorder. Cognitive disorders may to some extend be secondary to depression in the sense that an improvement in the depressive state will also lead to an improvement of the cognitive impairment. However, there is also clear evidence that cognitive disorders are, indeed, independent from depression. For instance, studies have shown persistent cognitive impairment upon recovery from depression [*J. Nervous Mental Disease*, 185, 748-754, 1997]. Moreover, the differential effect of antidepressants on depression and cognitive impairments lends further support to the notion that depression and cognitive impairment are independent, albeit often co-morbid conditions. While serotonin and noradrenalin medicaments provide comparable improvements in depressive symptoms, several studies have shown that modulation of the noradrenergic system does not improve the cognitive functions as much as serotonin modulation [*Brain Res. Bull.*, 58, 345-350, 2002; *Hum Psychpharmacol.*, 8, 41-47, 1993].

Cognitive functions are often impaired in schizophrenic patients, and may form part of the so-called negative symptoms of schizophrenia. Cognitive functions are also impaired in ADHD patients.

Cognitive deficits or cognitive impairment include a decline in cognitive functions or cognitive domains, e.g., working memory, attention and vigilance, verbal learning and memory, visual learning and memory, reasoning and problem solving, e.g., executive function, speed of processing and/or social cognition. In particular, cognitive deficits or cognitive impairment may indicate deficits in attention, disorganized thinking, slow thinking, difficulty in understanding, poor concentration, impairment of problem solving, poor memory, difficulties in expressing thoughts and/or difficulties in integrating thoughts, feelings and behaviour, or difficulties in extinction of irrelevant thoughts. The terms "cognitive deficits" and "cognitive impairment" are intended to indicate the same and are used interchangeably.

Data presented in example 4 shows that compound I is useful in the treatment of pain, and that it may even have an analgesic effect; additional studies in an animal model of neuropathic pain confirm this observation. Hence, compound I may be useful in the treatment of pain and affective or mood disorders, such as depression and anxiety associated with pain, and in particular chronic pain. Chronic pain includes indications such as phantom limb pain, neuropathic pain, diabetic neuropathy, post-herpetic neuralgia (PHN), carpal tunnel syndrome (CTS), tasus tunnel syndrome, ulnar nerve entrapment, spinal compression, HIV neuropathy, complex regional pain syndrome (CPRS), trigeminal neuralgia/trigeminus neuralgia/tic douloureux, surgical intervention (e.g., post-operative analgesics), diabetic vasculopathy, capillary resistance or diabetic symptoms associated with insulitis, pain associated with angina, pain associated with menstruation, pain associated with cancer, dental pain, headache, migraine, tension-type headache, trigeminal neuralgia, temporomandibular joint syndrome, myofascial pain muscular injury, fibromyalgia syndrome, bone and joint pain (osteoarthritis), rheumatoid arthritis, rheumatoid arthritis and edema resulting from trauma associated with burns, sprains or fracture of bone, pain due to osteoarthritis, osteoporosis, bone metastases or unknown reasons, gout, fibrositis, myofascial pain, thoracic outlet syndromes, upper back pain or lower back pain (wherein the back pain results from systematic, regional, or primary spine disease (radiculopathy), pelvic pain, cardiac chest pain, non-cardiac chest pain, spinal cord injury (SCI)-associated pain, central post-stroke pain, cancer neuropathy, AIDS pain, sickle cell pain, whiplash and geriatric pain.

Compound I has been tested in clinical trials using HAM-D (Hamilton Rating Scale for Depression) as clinical end-point. The HAM-D scale may be used to assess the severity of depression in patients by means of a 24 items questionnaire. Item 4, 5 and 6 of the scale relate to how the patients sleep, i.e., is it easy to fall asleep (insomnia Early), does the patient wake up during the night (Insomnia Middle), and does the patient wake up early in the morning (Insomnia Late). The compound was tested at 5 and 10 mg daily against placebo with approximately 100 patients per arm. The data in FIGS. 6-8 clearly show that compound I gives rise to a large and dose dependent improvement of the sleep pattern which is superior to that provided by placebo. It is well-known that sleep disturbances are a general adverse effect of most antidepressants. In particular SSRI's and compounds which inhibit the noradrenaline transporter are reported to give rise to problems with sleep initiation and maintenance and problems with insomnia are also often reported [*Int.Clin.Psychpharm.*, 21 (suppl 1), S25-S29, 2006]. Others report that such compounds give rise to suppressed REM sleep, increased sleep latency, less efficient sleep, increase in nocturnal awakenings, and fragmentation of sleep [*Hum.Psychopharm.Clin.Exp.*, 20, 533-559, 2005]. It is therefore a surprising result that the administration of compound I is not associated with adverse sleep effects, but in fact provides an improvement of the sleep pattern. Hence, the compound used in the present invention may be useful in the treatment of sleep disorders, such as difficulties in falling asleep, frequent nocturnal arousals and early morning awakenings.

The above mentioned clinical trial also captured sexual adverse effects reported by the patients. The table below shows the number of patients reporting the specified types of sexually related adverse effects.

| Adverse effect reported | Placebo | 5 mg | 10 mg |
| --- | --- | --- | --- |
| Anorgasmia | 0 | 0 | 0 |
| Ejaculation delayed | 0 | 0 | 0 |
| Erectile dysfunction | 0 | 0 | 0 |
| Libido decreased | 0 | 1 | 1 |
| Orgasm abnormal | 2 | 0 | 0 |
| Loss of libido | 0 | 1 | 0 |
| Orgasmic sensation decreased | 0 | 0 | 0 |

It is well known that treatment with anti-depressants in general and SSRI's in particular may be associated with sexual dysfunction and which frequently leads to discontinuation of the treatment. As much as 30-70% of patients on SSRIs report deficits in sexual function [*J.Clin.Psych.*, 66, 844-848, 2005], which deficits include decreased libido, delayed, reduced or absent orgasms, diminished arousal, and erectile dysfunction. The above results which show that the sexual adverse effect of compound I is similar to placebo is thus much better than what would normally be expected from an antidepressant, and in particular an SSRI. The compounds used in the present invention may be useful in the treatment of sexual dysfunctions, such as anorgasmia, delayed ejaculation, erectile dysfunction, decreased libido, abnormal orgasm, loss of libido or decreased orgasmic sensation.

Adverse effects which disrupt sleep and sexual activity may be very difficult to accept for patients and in particular patient on long term, not to mention chronic treatment, and they may cause treatment drop outs. The absence of these adverse effects in treatments comprising the administration of compound I makes compound I particular useful in therapeutic interventions over an extended period of time, such as depression relapse prevention.

The beneficial effects on the sleep pattern brought about by compound I makes it particular attractive to use compound I as described herein in the treatment of patients who already have problems with sleeping or suffer from a sleep disorder or in patients with sexually related disorders.

The compounds used in the present invention may also be useful as second line treatment for patients who cannot use other drugs, such as other anti-depressants, such as selective serotonin reuptake inhibitors (SSRI), selective noradrenalin reuptake inhibitors (NRI), noradrenaline/serotonin reuptake inhibitors (SNRI) or tri-cyclics (TCA) due to sleep or sexually related adverse events. In this embodiment, the patient to be treated has received another medication (or is still receiving it), which medication was ceased or reduced (or has to be ceased or reduced) due to sleep or sexually related adverse events. Typically, the patient is suffering from mood disorders, such as depression and anxiety, abuse (alcohol, narcotics etc) or chronic pain disorders.

The unique pharmacological profile of compound I combined with an unexpectedly favourable safety profile makes compound I useful in the treatment of, e.g., circadian rhythm disorder, sleep disorders, sleep-disordered breathing; hypopnea syndrome; abdominal pain; depression, in particular severe depression; dysthymic disorder; cyclothymia; exhaustive depression; atypical depression; mood disorder associated with a generalised medical disorder; substance induced mood disorder; recurrent depression, single episode depression; paediatric depression; post-stroke depression; per-, pre- or post-menopausal dysphoric disorder; seasonal affective disorder (SAD); aggression and agitation in dementia, such as Alzheimer's; compulsive and attention spectrum disorders in ADHD, autism and Asperger's syndrome; leucariosis, small vessel disease, depression associated with abuse, irritability, hostility, sleep disorders, fatigue, Huntington's disease, multiple sclerosis, anxiety (anxious depression) and pain, in particular pain in the gastrointestinal tract, such as e.g. irritable bowl syndrome (IBS); general anxiety disorder associated with pain; impulse control disease; intermittent explosive disorder; kleptomania; pyromania; pathological gambling; trichotillomania; negative symptoms of schizophrenia; mild cognitive impairment; vascular dementia; cognitive impairment associated with Down's syndrome, tph gene mutations, ADHD, epilepsy, traumatic brain injury or Asperger's syndrome; compulsive and attention spectrum disorder in ADHD, Asperger's syndrome and autism; aggression and agitation in dementia and Alzheimer's, disease; chronic fatigue syndrome; stress related disorder, acute stress; stress; burn-out; insulin resistance associated with HPA-axis hyperactivity; eating disorder, such as obesity, binge eating, anorexia and bulimia nervosa; conduct disorder; behavioural disturbances; behavioural disturbances associated with dementia; fear of flying; fear of elevators; fear of small rooms; and amblyopia. The treatment of these diseases by the administration of compound I is particularly useful and beneficial because it is expected to be without sexual and sleep related adverse effects and because an effect on cognitive impairment, which is associated with many of the above mentioned diseases, is expected, too.

In this context "severe depression" is depression wherein the patient scores above 30, such as above 32 or above 35 on the MADRS scale.

In one embodiment, the invention relates to a method of treating a diseases selected from circadian rhythm disorder; difficulties in falling asleep; nocturnal arousals; early morning awakenings; sleep-disordered breathing; hypopnea syndrome; severe depression; dysthymic disorder; cyclothymia; exhaustive depression; atypical depression; mood disorder associated with a generalised medical disorder; substance induced mood disorder; recurrent depression; single episode depression; paediatric depression; post-stroke depression; peri-, pre- or post-menopausal dysphoric disorder; seasonal affective disorder (SAD); aggression and agitation in dementia or Alzheimer's disease; compulsive and attention spectrum disorders in ADHD, autism or Asperger's syndrome; leucariosis; small vessel disease; depression associated with abuse, irritability, hostility, sleep disorders, fatigue, Huntington's disease, multiple sclerosis, anxiety (anxious depression), pain, pain in the gastrointestinal tract or irritable bowl syndrome (IBS); general anxiety disorder associated with pain; impulse control disease; intermittent explosive disorder; kleptomania; pyromania; pathological gambling; trichotillomania; negative symptoms of schizophrenia; mild cognitive impairment; vascular dementia; cognitive impairment associated with Down's syndrome, tph gene mutations, ADHD, epilepsy, traumatic brain injury or Asperger's syndrome; aggression and agitation in dementia and Alzheimer's disease; chronic fatigue syndrome; stress related disorder; acute stress; stress; burn-out; insulin resistance associated with HPA-axis hyperactivity; obesity; binge eating; anorexia; bulimia nervosa; conduct disorder; behavioural disturbances; behavioural disturbances in the elderly; fear of flying; fear of elevators; fear of small rooms; amblyopia; anorgasmia; delayed ejaculation; erectile dysfunction; decreased libido; abnormal orgasm; loss of libido; or decreased orgasmic sensation, the method comprising the administration of a therapeutically effective amount of compound I to a patient in need thereof.

In one embodiment, the patient to be treated has been diagnosed with the disease said patient is being treated for.

In one embodiment, the patient to be treated has previously received medication, such as another anti-depressant, such as selective serotonin reuptake inhibitors (SSRI), selective noradrenalin reuptake inhibitors (NRI), noradrenaline/serotonin reuptake inhibitors (SNRI) or tri-cyclics (TCA) for the treatment of said disease (or is still receiving it), which medication was ceased or reduced (or has to be ceased or reduced) due to sleep or sexually related adverse events. In this embodiment, the compounds used in the present invention are administered as second-line treatment.

A "therapeutically effective amount" of a compound as used herein means an amount sufficient to cure, alleviate or partially arrest the clinical manifestations of a given disease and its complications in a therapeutic intervention comprising the administration of said compound. An amount adequate to accomplish this is defined as "a therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatment are two separate aspects of the invention. The patient to be treated is preferably a mammal, in particular a human being.

Typically, the treatment of the present invention will involve daily administration of the compounds of the present invention. This may involve once daily administration, or administration twice a day or even more frequently.

In one embodiment, the invention relates to the use of compound I in the manufacture of a medicament for the treatment of a diseases selected from circadian rhythm disorder; difficulties in falling asleep; nocturnal arousals; early morning awakenings; sleep-disordered breathing; hypopnea syndrome; severe depression; dysthymic disorder; cyclothymia; exhaustive depression; atypical depression; mood disorder associated with a generalised medical disorder; substance induced mood disorder; recurrent depression; single episode depression; paediatric depression; post-stroke depression; peri-, pre- or post-menopausal dysphoric disorder; seasonal affective disorder (SAD); aggression and agitation in dementia or Alzheimer's disease; compulsive and attention spectrum disorders in ADHD, autism or Asperger's syndrome; leucariosis; small vessel disease; depression associated with abuse, irritability, hostility, sleep disorders, fatigue, Huntington's disease, multiple sclerosis, anxiety (anxious depression), pain, pain in the gastrointestinal tract or irritable bowl syndrome (IBS); general anxiety disorder associated with pain; impulse control disease; intermittent explosive disorder; kleptomania; pyromania; pathological gambling; trichotillomania; negative symptoms of schizophrenia; mild cognitive impairment; vascular dementia; cognitive impairment associated with Down's syndrome, tph gene mutations, ADHD, epilepsy, traumatic brain injury or Asperger's syndrome; aggression and agitation in dementia and Alzheimer's disease; chronic fatigue syndrome; stress related disorder; acute stress; stress; burn-out; insulin resistance associated with HPA-axis hyperactivity; obesity; binge eating; anorexia; bulimia nervosa; conduct disorder; behavioural disturbances; behavioural disturbances in the elderly; fear of flying; fear of elevators; fear of small rooms; amblyopia; anorgasmia; delayed ejaculation; erectile dysfunction;

decreased libido; abnormal orgasm; loss of libido; or decreased orgasmic sensation. In one embodiment, the medicament is for use in a patient who previously received (or is still receiving) another medication, such as another anti-depressant, such as selective serotonin reuptake inhibitors (SSRI), selective noradrenalin reuptake inhibitors (NRI), noradrenaline/serotonin reuptake inhibitors (SNRI) or tri-cyclics (TCA) for the treatment of said disease, which medication was ceased or reduced (or has to be ceased or reduced) due to sleep or sexually related adverse events.

In one embodiment, the invention relates to compound I for use in the treatment of a disease selected from circadian rhythm disorder; difficulties in falling asleep; nocturnal arousals; early morning awakenings; sleep-disordered breathing; hypopnea syndrome; severe depression; dysthymic disorder; cyclothymia; exhaustive depression; atypical depression; mood disorder associated with a generalised medical disorder; substance induced mood disorder; recurrent depression; single episode depression; paediatric depression; post-stroke depression; peri-, pre- or post-menopausal dysphoric disorder; seasonal affective disorder (SAD); aggression and agitation in dementia or Alzheimer's disease; compulsive and attention spectrum disorders in ADHD, autism or Asperger's syndrome; leucariosis; small vessel disease; depression associated with abuse, irritability, hostility, sleep disorders, fatigue, Huntington's disease, multiple sclerosis, anxiety (anxious depression), pain, pain in the gastrointestinal tract or irritable bowel syndrome (IBS); general anxiety disorder associated with pain; impulse control disease; intermittent explosive disorder; kleptomania; pyromania; pathological gambling; trichotillomania; negative symptoms of schizophrenia; mild cognitive impairment; vascular dementia; cognitive impairment associated with Down's syndrome, tph gene mutations, ADHD, epilepsy, traumatic brain injury or Asperger's syndrome; aggression and agitation in dementia and Alzheimer's disease; chronic fatigue syndrome; stress related disorder; acute stress; stress; burn-out; insulin resistance associated with HPA-axis hyperactivity; obesity; binge eating; anorexia; bulimia nervosa; conduct disorder; behavioural disturbances; behavioural disturbances associated with dementia; behavioural disturbances in the elderly; fear of flying; fear of elevators; fear of small rooms; amblyopia; anorgasmia; delayed ejaculation; erectile dysfunction; decreased libido; abnormal orgasm; loss of libido; or decreased orgasmic sensation. In one embodiment, compound I is for use in a patient who previously received (or is still receiving) another medication, such as another anti-depressant, such as e.g. selective serotonin reuptake inhibitors (SSRI), selective noradrenalin reuptake inhibitors (NRI), noradrenaline/serotonin reuptake inhibitors (SNRI) or tri-cyclics (TCA) for the treatment of said disease, which medication was ceased or reduced (or has to be ceased or reduced) due to sleep or sexually related adverse events.

Compound I is conveniently presented in a pharmaceutical composition which may be prepared by conventional methods in the art. Particular mentioning is made of tablets, which may be prepared by mixing the active ingredient with ordinary adjuvants and/or diluents and subsequently compressing the mixture in a conventional tabletting machine. Examples of adjuvants or diluents comprise: anhydrous calcium hydrogen phosphate, PVP, PVP-VA co-polymers, microcrystalline cellulose, sodium starch glycolate, corn starch, mannitol, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilising the solution and filling it in suitable ampoules or vials. Any suitable additive conventionally used in the art may be added, such as tonicity agents, preservatives, antioxidants, etc.

The pharmaceutical compositions manufactured in accordance with this invention may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients or other additives normally used in the art may be used.

Conveniently, compound I is administered in unit dosage form containing said compound in an amount of about 1 to 50 mg. An upper limit is believed to be set by the concentration dependency of the $5\text{-}HT_3$ activity. The total daily dose is usually in the range of about 1-20 mg, such as about 1 to 10 mg, about 5-10 mg, about 10-20 mg, or about 10-15 mg of the compound of the invention. Particular mention is made of daily doses of 2.5, 5, 10, 15 or 20 mg.

Tablets comprising a compound I may conveniently be prepared by wet granulation. Using this method, the dry solids (active ingredients, filler, binder etc.) are blended and moistened with water or another wetting agent (e.g. an alcohol) and agglomerates or granules are built up of the moistened solids. Wet massing is continued until a desired homogenous particle size has been achieved whereupon the granulated product is dried. Compound I is typically mixed with lactose monohydrate, corn starch and copovidone in a high shear mixer together with water. Following formation of granulates, these granulates may be sieved in a sieve with a suitable sieve size, and dried. The resulting dried granulates are then mixed with microcrystalline cellulose, croscarmellose sodium and magnesium stearate, following which the tablets are pressed. Alternatively, wet granulation of the compounds of the present invention may be achieved using mannitol, corn starch and copovidone, which granulates are mixed with microcrystalline cellulose, sodium starch glycolate and magnesium stearate before tablets are pressed. Alternatively, wet granulation of compound I may be achieved by using anhydrous calcium hydrogen phosphate, corn starch and copovidone, which granulates are mixed with microcrystalline cellulose, sodium starch glycolate (type A), talc and magnesium stearate before tablets are pressed. Copovidone is a PVP-VA copolymer.

In one embodiment, compound I is the hydrobromide salt, e.g., in the beta form, and suitable tablets may be composed as follows—percentages indicated are w/w-%

| | |
|---|---|
| HBr salt | 3-8% |
| Anhydrous calcium hydrogen phosphate | 35-45% |
| Corn starch | 15-25% |
| Copovidone | 2-6% |
| Microcrystalline cellulose | 20-30% |
| Sodium starch glycolate | 1-3% |
| Talc | 2-6% |
| Magnesium stearate | 0.5-2% |

In particular, the tablets may be composed as follows

| | |
|---|---|
| HBr salt | approximately 5% |
| Anhydrous calcium hydrogen phosphate | approximately 39% |
| Corn starch | approximately 20% |
| Copovidone | approximately 3% |
| Microcrystalline cellulose | approximately 25% |
| Sodium starch glycolate | approximately 3% |
| Talc | approximately 4% |
| Magnesium stearate | approximately 1% |

Tablets with different amounts of active compound, such as corresponding to e.g. 2.5, 5, 10, 20, 25, 30, 40, 50, 60 or 80 mg of the free base may be obtained by choosing the right amount of the compound I in combination with a tablet of an appropriate size.

Compound I may either be administered alone or in combination with another therapeutically active compound, wherein the two compounds may either be administered simultaneously or sequentially. Examples of therapeutically active compounds which may advantageously be combined with compound I include sedatives or hypnotics, such as benzodiazepines; anticonvulsants, such as lamotrigine, valproic acid, topiramate, gabapentin, carbamazepine; mood stabilizers such as lithium; dopaminergic drugs, such as dopamine agonists and L-Dopa; drugs to treat ADHD, such as atomoxetine; psychostimulants, such as modafinil, ketamine, methylphenidate and amphetamine; other antidepressants, such as mirtazapine, mianserin and buproprion; hormones, such as T3, estrogen, DHEA and testosterone; atypical antipsychotics, such as olanzapine and aripiprazole; typical antipsychotics, such as haloperidol; drugs to treat Alzheimer's diseases, such as cholinesterase inhibitors and memantine, folate; S-Adenosyl-Methionine; immunomodulators, such as interferons; opiates, such as buprenorphins; angiotensin II receptor 1 antagonists (AT1 antagonists); ACE inhibitors; statins; and alpha1 adrenergic antagonist, such as prazosin.

The free base of compound I may be prepared as disclosed in WO 2003/029232 or WO 2007/144005. Salts used in the present invention may be prepared by dissolving the free base in an appropriate solvent, adding the relevant acid, followed by precipitation. Precipitation may be accomplished either by the addition of a second solvent, and/or evaporation, and/or cooling. Alternatively, the free base used in the present invention may be synthesised in a palladium catalysed reaction as described in the examples.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various compounds of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

EXAMPLES

Analytical Methods $^1$H NMR spectra are recorded at 500.13 MHz on a Bruker Avance DRX500 instrument. Dimethyl sulfoxide (99.8% D) is used as solvent, and tetramethylsilane (TMS) is used as internal reference standard.

The melting points are measured using Differential Scanning Calorimetry (DSC). The equipment is a TA-Instruments DSC-Q1000 calibrated at 5°/min to give the melting point as onset value. About 2 mg of sample is heated 5°/min in a loosely closed pan under nitrogen flow.

Thermo gravimetric analysis (TGA) used for estimation of solvent/water content of dried material is performed using a TA-instruments TGA-Q500. 1-10 mg sample is heated 10°/min in an open pan under nitrogen flow.

X-Ray powder diffractograms were measured on a PANalytical X'Pert PRO X-Ray Diffractometer using CuK$_{\alpha 1}$ radiation. The samples were measured in reflection mode in the 2θ-range 5-40° using an X'celerator detector. The reflection values provided are ±0.1 (° 2θ).

Example 1 In Vitro Receptor Pharmacology

Rat serotonin transporter: IC$_{50}$ 5.3 nM (blockade of 5-HT uptake)

Human serotonin transporter: IC$_{50}$ 5.4 nM (blockade of 5-HT uptake)

Human 5-Ht$_{1a}$ receptor: K$_i$ 15 Nm with agonism (efficacy or intrinsic activity 96%)

Rat 5-HT$_3$ receptor: IC$_{50}$ 0.2 nM (antagonism in functional assay)

Human 5-HT$_{3A}$ receptor: IC$_{50}$ around 20 nM (antagonism in functional assay). At higher concentration, the compound exhibits agonistic activity with an ED$_{50}$ of 2.1 μM. The compound of the invention also showed high affinity for the human 5HT$_3$ receptor in an in vitro binding assay (Ki 4.5 nM).

Example 2a Preparation of the Free Base of Compound I 10 grams of 1-[2-(2,4-dimethylphenylsulfanyl)-phenyl] piperazine hydrobromide was treated with a stirred mixture of 100 ml 3 M NaOH and 100 ml ethyl acetate for 10 minutes. The organic phase was separated, washed with 100 ml 15%-wt NaCl (aq), dried over MgSO$_4$, filtered and concentrated in vacuum producing 7.7 gram (98%) of compound I base as a clear colourless oil.

NMR complies with structure.

Example 2b Preparation of Crystalline Base of Compound I 3.0 gram of 1-[2-(2,4-dimethylphenylsulfanyl)-phenyl]piperazine colourless oil was treated with 70 ml acetonitrile and heated to reflux. The almost clear solution was filtered and the clear filtrate was cooled spontaneously upon which precipitation began shortly after filtration. The mixture was stirred at room temperature (22° C.) for 2 hours and the product was isolated by filtration and dried in vacuum (40° C.) overnight. The crystalline base was isolated as a white solid in 2.7 gram (90%). NMR complies with structure. Elemental analysis: 72.40% C, 9.28% N, 7.58% H (theory: 72.26% C, 9.36% N, 7.42% H)

Example 2c Characterisation of Crystalline Base of Compound I

The base, as prepared in Example 2b, is crystalline (XRPD)—see FIG. 1. It has a melting point of 117° C. It is not hygroscopic and has a solubility of 0.1 mg/ml in water.

Example 2d Preparation of the Alpha Form of the Hydrobromide Salt of Compound I 2.0 gram of 1-[2-(2,4-Dimethylphenylsulfanyl)-phenyl]piperazine was dissolved in hot 30 ml ethyl acetate and added 0.73 ml 48%-wt HBr (aq). This addition caused formation of a thick slurry and additional 10 ml ethyl acetate was added in order to have proper stirring. The slurry was stirred at room temperature for one hour. Filtration and drying in vacuum (20° C.) over night produced 2.0 gram of the product as a white solid (80%). NMR complies with structure. Elemental analysis: 57.05% C, 7.18% N, 6.16% H (Theory for 1:1 salt: 56.99% C, 7.39% N, 6.11% H)

Example 2e Characterisation of the Alpha Form of the Hydrobromide of Compound I The alpha form of the hydrobromide, as prepared in Example 2d, is crystalline (XRPD)—see FIG. 2. It has a melting point of ~226° C. It absorbs about 0.3% of water when exposed to high relative humidity and has a solubility of 2 mg/ml in water.

Example 2f Preparation of the Beta Form of the Hydrobromide Salt of Compound I 49.5 gram of 1-[2-(2,4-Dimethylphenylsulfanyl)-phenyl]piperazine colourless oil was dissolved in 500 ml ethyl acetate and added 18.5 ml 48%-wt HBr (aq). This addition caused formation of a thick slurry which was stirred over night at room temperature. Filtration and drying in vacuum (50° C.) over night produced the product in 29.6 gram as white solid (47%).

NMR complies with structure. Elemental analysis: 56.86% C, 7.35% N, 6.24% H (Theory for 1:1 salt: 56.99% C, 7.39% N, 6.11% H)

Example 2g Characterisation of the Beta Form of the Hydrobromide Salt of Compound I The beta form of the hydrobromide, as prepared in Example 2f, is crystalline (XRPD) see FIG. 3. It has a melting point of ~231° C. It absorbs about 0.6% of water when exposed to high relative humidity and has a solubility of 1.2 mg/ml in water.

Example 2h Preparation of the Gamma Form of the Hydrobromide Salt of Compound I 1 g of 1-[2-(2,4-Dimethylphenylsulfanyl)-phenyl]piperazine hydrobromide as prepared in Example 2d was added 20 ml water and heated to 85° C. The solution was almost clear. Addition of 1 drop of HBr made it clear. HBr was added until cloud point was observed. The solution was cooled to room temperature and dried. NMR complies with structure. Elemental analysis: 56.63% C, 7.18% N, 6.21% H (Theory for 1:1 salt: 56.99% C, 7.39% N, 6.11% H)

Example 2i Characterisation of the Gamma Form of the Hydrobromide of Compound I The hydrobromide, as prepared in Example 2h is crystalline (XRPD)—see FIG. 4. The DSC curve shows some thermal events at about 100° C.; probably change in crystal form. Then it melts at about 220° C. It absorbs about 4.5% of water when exposed to high relative humidity and at 30% RH at room temperature about 2% of water is absorbed.

Example 2j Preparation of the Hydrobromide Hydrate of Compound I 1.4 gram of 1-[2-(2,4-Dimethylphenylsulfanyl)-phenyl]piperazine oil was added 20 ml water, and heated to 60° C. pH was adjusted to 1 using 48% HBr. The solution was cooled to room temperature and dried. NMR complies with structure. Elemental analysis: 55.21% C, 7.16% N, 6.34% H (Theory for 1:1 salt hemihydrate: 55.68% C, 7.21% N, 6.23% H)

Example 2k Characterisation of the Hemi Hydrate of the Hydrobromide of Compound I The hydrate as prepared in Example 2j is crystalline (XRPD)—see FIG. 5. The water content depends strongly on the relative humidity. At room temperature and 95% RH the water content is about 3.7%. Dehydration occurs by heating to about 100° C.

Example 3 Preparation of Compound I

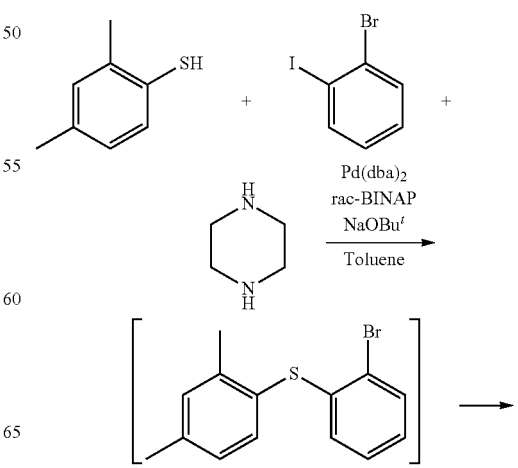

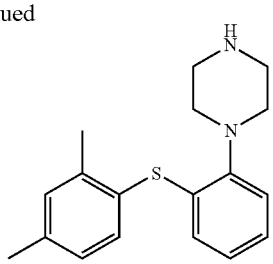

815 g NaOBu$^t$ (8.48 mol), 844 g piperazine (9.8 mol), 6.6 g Pd(dba)$_2$ (11.48 mmol) and 13.6 g rac-BINAP (21.84 mmol) were stirred with 4 L toluene for 50 minutes. 840 g 2-bromo-iodobenzene (2.97 mol) was then added along with 1.5 L toluene and stirring continued for 30 min. 390.8 g 2,4-dimethylthiophenol (2.83 mol) was finally added with 1.5 L toluene. The suspension was heated to reflux and reflux continued for 5 hours. The reaction mixture was cooled down over night. 2 L water was added and stirred for 1 hour before the mixture was filtrated through filter aid. The filtrate was then washed with 3×1 L brine. The combined water phases were then extracted with 600 ml toluene. The combined toluene phases were then heated to 70° C. followed by addition of 329.2 ml 48-wt % HBr (aq.) and 164.6 ml water. The mixture was cooled to room temperature over night. The final product (1-[2-(2,4-Dimethyl-phenylsulfanyl)-phenyl]-piperazine hydrobromide) was collected by filtration and dried in vacuum (60° C.) producing 895 g (84% yield).

Example 4 Pain Effects in the Mouse Intradermal Formalin Test

In this model, mice receive an injection of formalin (4.5%, 20 µl) into the left hind paw. The irritation caused by the formalin injection elicits a characteristic biphasic behavioural response, as quantified by the amount of time spent licking the injured paw.

The first phase (~0-10 minutes) represents direct chemical irritation and nociception, whereas the second phase (~20-30 minutes) is thought to represent pain of neuropathic origin. The two phases are separated by a quiescent period in which behaviour returns to normal. The effectiveness of test compounds to reduce the painful stimuli is assessed by counting the amount of time spent licking the injured paw in the two phases.

Compound I showed a significant reduction in second phase pain scores (FIG. 9a), indicating efficacy against pain of neuropathic origin. Furthermore, the compounds of the present invention showed a significant reduction in the first phase scores (FIG. 9b), indicating a more analgesic action at the highest dose. In summary, these results indicate that compounds of the present invention are likely to be effective in the treatment of pain disorders.

Example 5 Effects on Extracellular Levels of Acetylcholine in the Brain of Freely Moving Rats The animals were administered 1-[2-(2,4-dimethylphenylsulfanyl)phenyl]piperazine, HBr salt.
Animals
Male Sprague-Dawley rats, initially weighing 275-300 g, were used. The animals were housed under a 12-hr light/dark cycle under controlled conditions for regular in-door temperature (21±2° C.) and humidity (55±5%) with food and tap water available ad libitum.

Surgery and Microdialysis Experiments

Rats were anaesthetised with hypnorm/dormicum (2 ml/kg) and intracerebral guide cannulas (CMA/12) were stereotaxically implanted into the brain, aiming at positioning the dialysis probe tip in the ventral hippocampus (co-ordinates: 5.6 mm posterior to bregma, lateral −5.0 mm, 7.0 mm ventral to dura) or in the prefrontal cortex (co-ordinates: 3.2 mm anterior to bregma; lateral, 0.8 mm; 4.0 mm ventral to dura). Anchor screws and acrylic cement were used for fixation of the guide cannulas. The body temperature of the animals was monitored by rectal probe and maintained at 37° C. The rats were allowed to recover from surgery for 2 days, housed singly in cages. On the day of the experiment a microdialysis probe (CMA/12, 0.5 mm diameter, 3 mm length) was inserted through the guide cannula.

The probes were connected via a dual channel swivel to a microinjection pump. Perfusion of the microdialysis probe with filtered Ringer solution (145 mm NaCl, 3 mM KCl, 1 mM MgCl$_2$, 1.2 mM CaCl$_2$) containing 0.5 µM neostigmine) was begun shortly before insertion of the probe into the brain and continued for the duration of the experiment at a constant flow rate of 1 µl/min. After 180 min of stabilisation, the experiments were initiated. Dialysates were collected every 20 min. After the experiments the animals were sacrificed, their brains removed, frozen and sliced for probe placement verification.

The compound dissolved in 10% HPbetaCD and injected subcutaneously (2.5-10 mg/kg). Doses are expressed as mg salt/kg body weight. The compound was administered in a volume of 2.5 ml/kg.

Analysis of Dialysate Acetylcholine

Concentration of acetylcholine (ACh) in the dialysates was analysed by means of HPLC with electrochemical detection using a mobile phase consisting of 100 mM disodium hydrogenphosphate, 2.0 mM octane sulfonic acid, 0.5 mM tetramethylammonium chloride and 0.005% MB (ESA), pH 8.0. A pre-column enzyme reactor (ESA) containing immobilised choline oxidase eliminated choline from the injected sample (10 µl) prior to separation of ACh on the analytical column (ESA ACH-250); flow rate 0.35 ml/min, temperature: 35° C. After the analytical column the sample passed through a post-column solid phase reactor (ESA) containing immobilised acetylcholineesterase and choline oxidase. The latter reactor converted ACh to choline and subsequently choline to betaine and $H_2O_2$. The latter was detected electrochemical by using a platinum electrode (Analytical cell: ESA, model 5040).

Data Presentation

In single injection experiments the mean value of 3 consecutive ACh samples immediately preceding compound administration served as the basal level for each experiment and data were converted to percentage of basal (mean basal pre-injection values normalized to 100%).

Results

The compound significantly increased extra-cellular levels of ACh in the rat prefrontal cortex and the ventral hippocampus—see FIGS. 10a and 10b.

Example 6 Contextual Fear Conditioning in Rats

The compound administered in the present experiment was 1-[2-(2,4-dimethylphenyl-sulfanyl)phenyl]piperazine HBr salt.

We have studied the effect of the compound on acquisition, consolidation and recall of contextual fear conditioning in rats. In the fear conditioning paradigm animals learn to associate a neutral environment (context, the training chamber, CS) with an aversive experience (an electrical footshock, US). During re-exposure to the training chamber, animals express a freezing behaviour, which is taken as a direct measure of the fear-related memory [Pavlov J. Biol. Sci., 15, 177-182, 1980]. The neuroanatomy of contextual fear conditioning has been thoroughly investigated and several studies have demonstrated that the hippocampus and amygdala are necessary for the formation of this memory [*Hippocampus,* 11, 8-17, 2001; *J. Neurosci.,* 19, 1106-1114, 1999; *Behav. Neurosci.,* 106, 274-285, 1992].

Animals and Drugs

Adult male Sprague-Dawley rats (weighing 250-300 g at time of training) from Charles River Laboratories, housed two per cage under a 12 h light/dark cycle, were used. Food and water were available ad libitum. Rats were used 1 week after arrival. The compound was dissolved in 10% HPbetaCD and injected subcutaneously. The drug was administered in a volume of 2.5 ml/kg.

Apparatus

Training and testing were conducted in a soundproof chamber (30×20×40 cm) housed in an isolated room and connected to a ventilation system. Illumination was provided by a white light (60 Watt). The floor of the chamber consisted of a metal grid attached to an electric shock generator. Prior to training and testing, the chamber was cleaned with a 70% ethanol solution. A video camera allowed for behavioral observations and recording of the training session for off-line analysis.

Acquisition and Retention Test

During the acquisition animals were allowed to freely explore the novel environment for a 1 min habituation period, which co-terminated with one inescapable footshock (unconditioned stimulus, US) through the electrifiable grid floor. The foot shock had a duration of 2 s and an intensity of 0.75 mA. Animals remained in the conditioning chamber for another 60 s after the US. Freezing behaviour was scored during the first 58 s (pre-shock acquisition; experimenter blinded to groups) to determine baseline-freezing responses to the context. At the end of the acquisition animals were gently removed and placed into their home cages. After 24 h the same animals were reintroduced into the training context (fear conditioning chamber) and a 2 min retention test was performed. During this period no foot shocks were applied. Freezing behaviour was scored during the whole test period with the experimenter blinded to groups and presented as percent of total test period.

Results and Discussion

The effect of the compound on contextual fear conditioning in rats was studied (i) on acquisition (drug applied before acquisition, FIG. 11), (ii) on memory recall (drug applied before test, FIG. 12) and (iii) on consolidation (drug applied immediately after the acquisition, FIG. 13). In the first set of experiments, the compound (1, 5 and 10 mg/kg) was administered 1 h prior to the acquisition session. FIG. 11 depicts the acquisition of freezing behavior during training (58 s prior to the food shock) and the retention test 24 after. The following findings were observed:

The compound does not affect baseline freezing behaviour before the presentation of the foot shock at any dose tested.

The compound at 5 mg/kg has a tendency to increase the time spent freezing during the retention test, 24 h after the acquisition ($39.24 \pm 13.76\%$, n=6, versus $24.30 \pm 4.40\%$, n=16, in the vehicle-treated animals).

The compound at 10 mg/kg significantly increases the time spent freezing during the retention test, 24 h after the acquisition ($52.15 \pm 5.68\%$, n=10, versus $24.30 \pm 4.40\%$, n=16, in the vehicle-treated animals, $p<0.01$).

The fear conditioning model, as described in FIG. 11, is a standard procedure described in the literature for the investigation of learning and memory. In order to further elucidate the acute effects of this drug on memory recall, the compound (5, 10 and 20 mg/kg) was applied 1 h prior to the retention test. It was observed that the compound inhibits the expression of freezing behaviour at 5 mg/kg during the memory test ($12.86 \pm 3.57\%$, n=9, versus $33.61 \pm 4.29\%$, n=13, in the vehicle-treated animals, $p<0.05$) (FIG. 13).

As described above, the compound by itself does not affect baseline freezing behaviour before the onset of US (FIG. 11), thus the most plausible hypothesis is that the observed effect in FIG. 12 is due to an anxiolytic effect. The conditioned memory is assessed via freezing behaviour, a response that is reduced by compounds with potential anxiolytic effects. This experiment demonstrates that the compound given acutely before memory recall has anxiolytic efficacy, it is therefore unlikely that increased freezing shown in FIG. 11 is due to an anxiogenic effect of the compound.

In order to strengthen that the compound is not anxiogenic but bears pro-cognitive potential, the compound was administered at 5, 10 and 20 mg/kg after the acquisition session. Consequently, in this set of experiments, the compound was onboard neither during the acquisition nor throughout the retention test. Here, it was observed that the compound at 5 mg/kg significantly enhances the time spent freezing during the retention test, 24 h after the acquisition session ($45.58 \pm 4.50\%$, n=8, versus $25.26 \pm 3.57\%$, n=19, in the vehicle-treated animals, $p<0.05$). The percentage of time spent freezing during the context re-exposure has been described as a measure of a fear-related memory [*Pavlov J. Biol. Sci,* 15, 177-182, 1980], which is enhanced in compound-treated rats when compared to vehicle-treated animals (FIGS. 11 and 12). Taken together, the data show that the compound enhances contextual memory.

The invention claimed is:

1. A method of treating mild cognitive impairment, the method comprising administering to a patient in need thereof a therapeutically effective amount of compound I, which is 1-[2-(2,4-dimethylphenylsulfanyl)phenyl]piperazine or a pharmaceutically acceptable salt thereof, to a patient in need thereof;

wherein said method alleviates a symptom or complication of mild cognitive impairment, or delays the progression of mild cognitive impairment in the patient.

2. The method according to claim 1, wherein the method comprises administering a hydrobromic acid salt of 1-[2-(2,4-dimethylphenylsulfanyl)phenyl]piperazine to the patient.

3. The method according to claim 2, wherein said hydrobromic acid salt is crystalline and said crystalline salt is characterized by having major XRDP peaks at 5.85, 9.30, 17.49 and 18.58 (° 2θ), all ±0.1 (° 2θ).

4. The method according to claim 2, wherein said hydrobromic acid salt is crystalline and said crystalline salt is characterized by having major XRDP peaks at 11.82, 16.01, 17.22 and 18.84 (° 2θ), all ±0.1 (° 2θ).

5. The method according to claim 2, wherein said hydrobromic acid salt is crystalline and said crystalline salt is characterized by having major XRDP peaks at 6.89, 9.73, 13.78 and 14.62 (° 2θ), all ±0.1 (° 2θ).

6. The method according to claim 5, wherein said hydrobromic acid salt is characterised by an XRDP as depicted in FIG. 3.

7. The method according to claim 1, wherein compound I is administered to the patient in unit doses of about 1-50 mg.

8. The method according to claim 2, wherein the patient is administered between about 1 and 20 mg per day of the hydrobromic acid salt of 1-[2-(2,4-dimethylphenylsulfanyl)phenyl]piperazine orally.

9. The method according to claim 1, wherein said patient is administered a therapeutically effective amount of compound I provided it is not the free base of 1-[2-(2,4-dimethylphenylsulfanyl)phenyl]piperazine in a non-crystalline form.

* * * * *